(12) United States Patent
Wada et al.

(10) Patent No.: US 11,459,431 B2
(45) Date of Patent: Oct. 4, 2022

(54) METHOD FOR PRODUCING POLYACRYLIC ACID (SALT)-BASED WATER ABSORBENT RESIN

(71) Applicant: NIPPON SHOKUBAI CO., LTD., Osaka (JP)

(72) Inventors: Hidenori Wada, Himeji (JP); Motohiro Imura, Himeji (JP); Katsuyuki Wada, Himeji (JP); Seiji Kato, Himeji (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 31 days.

(21) Appl. No.: 16/904,428

(22) Filed: Jun. 17, 2020

(65) Prior Publication Data
US 2020/0317872 A1    Oct. 8, 2020

Related U.S. Application Data

(62) Division of application No. 14/648,430, filed as application No. PCT/JP2013/082503 on Dec. 3, 2013, now abandoned.

(30) Foreign Application Priority Data

Dec. 3, 2012 (JP) ................. 2012-263962

(51) Int. Cl.
| | | |
|---|---|---|
| C08J 3/24 | (2006.01) | |
| C08J 3/075 | (2006.01) | |
| A61L 15/24 | (2006.01) | |
| A61L 15/42 | (2006.01) | |
| A61L 15/60 | (2006.01) | |

(52) U.S. Cl.
CPC .............. *C08J 3/245* (2013.01); *A61L 15/24* (2013.01); *A61L 15/42* (2013.01); *A61L 15/60* (2013.01); *C08J 3/075* (2013.01); *C08J 2333/02* (2013.01)

(58) Field of Classification Search
None
See application file for complete search history.

(56) References Cited

U.S. PATENT DOCUMENTS

| | | |
|---|---|---|
| 4,920,202 A | 4/1990 | Irie et al. |
| 5,096,944 A | 3/1992 | Itou et al. |
| 5,672,633 A | 9/1997 | Brehm et al. |
| 5,728,742 A | 3/1998 | Staples et al. |
| 5,994,440 A | 11/1999 | Staples et al. |
| 6,071,976 A | 6/2000 | Dairoku et al. |
| 6,090,875 A | 7/2000 | Staples et al. |
| 6,323,252 B1 | 11/2001 | Gartner et al. |
| 6,414,214 B1 | 7/2002 | Engelhardt et al. |
| 6,720,389 B2 | 4/2004 | Hatsuda et al. |
| 7,378,453 B2 | 5/2008 | Nogi et al. |
| 7,473,470 B2 | 1/2009 | Ishizaki et al. |
| 7,507,475 B2 | 3/2009 | Inger et al. |
| 8,299,207 B2 | 10/2012 | Wengeler et al. |
| 8,410,223 B2 | 4/2013 | Matsumoto et al. |
| 8,546,492 B2 | 10/2013 | Motoyama et al. |
| 2002/0061978 A1* | 5/2002 | Hatsuda .................. A61L 15/60 525/330.1 |
| 2004/0071966 A1 | 4/2004 | Inger et al. |
| 2004/0186244 A1 | 9/2004 | Hatsuda et al. |
| 2005/0209352 A1 | 9/2005 | Dairoku |
| 2007/0065503 A1 | 3/2007 | Harren |
| 2007/0066167 A1 | 3/2007 | Wada |
| 2007/0141338 A1 | 6/2007 | Ishizaki |
| 2009/0186542 A1 | 7/2009 | Kondo et al. |
| 2010/0323885 A1 | 12/2010 | Herfert et al. |
| 2011/0040044 A1* | 2/2011 | Motoyama .............. C08L 33/02 525/384 |
| 2011/0237739 A1 | 9/2011 | Tada et al. |
| 2011/0319518 A1 | 12/2011 | Kadonaga et al. |
| 2012/0172536 A1 | 7/2012 | Nogi et al. |
| 2012/0184670 A1 | 7/2012 | Kobayashi et al. |

(Continued)

FOREIGN PATENT DOCUMENTS

| | | |
|---|---|---|
| CN | 102574100 A | 7/2012 |
| EP | 1730218 B1 | 12/2010 |
| EP | 2995639 A1 | 3/2016 |

(Continued)

OTHER PUBLICATIONS

Amtliche Wetterdaten fur Nordrhein-Westfalen, abgrufen am Apr. 5, 2021 um 12:42 MESZ.

Veroffentlichung der Fa. Nihon Yamamura Glass Co.,Ltd. "Standard Bottles Catalogue 2020" abgerufen von https://www.yamamura.co.jp/english/business/pdf/Standard_Bottles_Catalogue_2020.pdf.

Produktinformation Z265950—Solid-glass beads von Merck KGaA, abgerufen von https://www.sigmaaldrich.com/catalog/product/aldrich/z265950?lang=de&region=DE.

Produktinformation Z143952—Solid-glass beads von Merck KGaA, abgerufen von https://www.sigmaaldrich.com/catalog/product/aldrich/z143952?lang=de&region=DE.

Moore, John H. Davis, Christopher C. Coplan, Michael A. Greer, Sandra C.. (2009). Building Scientific Apparatus (4th Edition)—2. 1.1 Chemical Composition and Chemical Properties of Some Laboratory Glasses. Cambridge University Press. Retrieved from https://app.knovel.com/hotlink/pdf/id:kt007RJWN2/building-scientific-apparatus/chemical-composition.

(Continued)

*Primary Examiner* — Tanisha Diggs
(74) *Attorney, Agent, or Firm* — Dickinson Wright PLLC

(57) ABSTRACT

As a method for producing a polyacrylic acid (salt)-based water absorbent resin particle which less generates fine powder and has an excellent impact resistance and a high moisture content even in a case where the polyacrylic acid (salt)-based water absorbent resin particle is produced on a large scale, employed is a production method including the steps of: (a) adding a surface crosslinking agent solution to water absorbent resin powder to obtain a mixture; (b) reacting the mixture; and, thereafter (c) adding an aqueous liquid to at least one selected from the group consisting of (i) the water absorbent resin powder during the step (b) and (ii) the water absorbent resin powder after the step (b), an atmospheric dew point being not lower than 20° C. in the step (c), and a temperature of the water absorbent resin powder being higher than the atmospheric dew point in the step (c).

10 Claims, No Drawings

(56) References Cited

U.S. PATENT DOCUMENTS

| | | |
|---|---|---|
| 2014/0193641 A1 | 7/2014 | Torii |
| 2014/0299815 A1 | 10/2014 | Ueda |

FOREIGN PATENT DOCUMENTS

| | | |
|---|---|---|
| JP | 03-195705 | 8/1991 |
| JP | 09-124879 | 5/1997 |
| JP | 2002-201290 A | 7/2002 |
| JP | 2008-533213 | 8/2008 |
| JP | 2011-213759 | 10/2011 |
| WO | 2006/101271 | 9/2006 |
| WO | 2009/125849 | 10/2009 |
| WO | 2011/040530 | 4/2011 |
| WO | 2012133734 A1 | 10/2012 |
| WO | 2013002387 A1 | 1/2013 |
| WO | 2013073614 A1 | 5/2013 |
| WO | 2014/041968 | 3/2014 |
| WO | 2014/041969 | 3/2014 |

OTHER PUBLICATIONS

European Notice of Opposition to Grant the Patent, dated May 25, 2021, which issued in the corresponding European Patent Application No. 13860396.4.
U.S. Office Action dated Apr. 3, 2020, which issued in the corresponding U.S. Appl. No. 14/648,430.
U.S. Advisory Action dated Mar. 16, 2020, which issued in the corresponding U.S. Appl. No. 14/648,430.
U.S. Office Action dated Sep. 27, 2019, which issued in the corresponding U.S. Appl. No. 14/648,430.
U.S. 1st Office Action, dated Dec. 26, 2018, which issued in the corresponding U.S. Appl. No. 14/648,430.
U.S. Final Office Action dated May 7, 2018, which issued in the corresponding U.S. Appl. No. 14/648,430.
U.S. Office Action dated Sep. 25, 2017, which issued in the corresponding U.S. Appl. No. 14/648,430.
U.S. Advisory Action dated Aug. 18, 2017, which issued in the corresponding U.S. Appl. No. 14/648,430.
U.S. Final Office Action dated Mar. 22, 2017, which issued in the corresponding U.S. Appl. No. 14/648,430.
U.S. Office Action dated Aug. 15, 2016, which issued in the corresponding U.S. Appl. No. 14/648,430.
International Preliminary Report on Patentability for PCT/JP2013/082503, dated Jun. 18, 2015.
International Search Report for PCT/JP2013/082503, dated Mar. 18, 2014.
International Search Report for PCT/JP2013/082503, dated Mar. 18, 2014, and English translation thereof.
Supplementary European Search Report dated Jun. 6, 2016 which issued in the corresponding Patent Application No. 13860396.4.
Chinese Office Action dated Jun. 1, 2016, issued in counterpart Patent Application No. 201380062783.X, incl. English Translation.
Japanese Office Action dated Dec. 8, 2015, issued in counterpart Patent Application No. 2014-551112.
Translation of WO 2011/040530 published Apr. 7, 2011.
Translation of JP 2011-213759 published Oct. 27, 2011.
Chinese Office Action dated Dec. 14, 2021, which issued in the corresponding Chinese Patent Application No. 201910814837.2, including Eng. translation.
Buchholz, Frederick L. et al.: Modern Superabsorbent Polymer Technology—Chapter 4: Analysis and Characterization of Superabsorbent Polymers (pp. 119-165) John Wiley & Sons, Inc.—copyright 1998.
Buchholz, Frederick L. et al.: Modern Superabsorbent Polymer Technology—Chapter 2: Chemistry of Superabsorbent Polyacrylates. pp. 19-67 John Wiley & Sons, Inc.—copyright 1998.

* cited by examiner

METHOD FOR PRODUCING POLYACRYLIC ACID (SALT)-BASED WATER ABSORBENT RESIN

This application is a divisional of U.S. patent application Ser. No. 14/648,430, filed May 29, 2015, which is based on PCT Application No. PCT/JP2013/082503, filed Dec. 3, 2013, which claims the benefit of Japanese Patent Application No. 2012-263962, filed Dec. 3, 2012, the entire contents of which are incorporated herein by reference.

TECHNICAL FIELD

The present invention relates to a method for producing a polyacrylic acid (salt)-based water absorbent resin. The present invention particularly relates to a method for producing a polyacrylic acid (salt)-based water absorbent resin, the method stably and continuously producing a water absorbent resin having a high moisture content and high performance by further adding an aqueous liquid to the water absorbent resin to/with which a surface crosslinking agent has been added and mixed.

BACKGROUND ART

A water absorbent resin (SAP/Super Absorbent Polymer) is a water-swellable water-insoluble polymer gelatinizer, and has a property of absorbing an aqueous liquid several times to several hundreds of times as heavy as its weight. Therefore, the water absorbent resin is widely used for (i) sanitary products such as disposable diapers, sanitary napkins and incontinence pads, (ii) an agriculture/horticulture water retaining agent, (iii) an industrial waterproofing agent, and the like.

For such water absorbent resin, many monomers and hydrophilic polymers have been proposed as raw materials. In terms of water absorbing ability, a polyacrylic acid (salt)-based water absorbent resin in which acrylic acid and/or its salt are/is used as its monomer is most popular in industries.

The water absorbent resin is required to have various functions (excellent physical properties) in order to cope with functional sophistication of disposable diapers which are one major application of the water absorbent resin. Specifically, the water absorbent resin is required to improve physical properties such as, not only basic physical properties, i.e., a water absorption capacity without load and a water absorption capacity under load, but also gel strength, water soluble component, moisture content, water absorbing speed, liquid permeability, particle size distribution, an anti-urine property, an antimicrobial property, an anti-damage property, powder fluidity, a deodorant property, an anti-coloring property, low dustiness, and low residual monomer. Therefore, there have been proposed various techniques for improving these physical properties. Specifically, Patent Literatures 1 through 20 and 23 through 25, and Patent Literatures 21 and 22 which have not been published disclose techniques for, for example, changing drying, surface crosslinking, an additive, or a production process.

As a technique for surface-crosslinking a water absorbent resin proposed are (i) a technique for adding, in the form of water vapor, part or all of water contained in a surface-crosslinking agent solution while carrying out humidification and blending (Patent Literature 1), (ii) a technique for controlling an atmospheric dew point in a heat treatment (Patent Literatures 2 and 19, and Patent Literatures 21 and 22 (filed by the applicant of the present application) which have not been published), (iii) a technique for defining a size of an apparatus for cooling a heated water absorbent resin (Patent Literature 3), (iv) a technique for reducing a residual crosslinking agent by further adding (5 wt % to 20 wt % of) an aqueous liquid during heating of a polymer whose moisture content falls within a range from 10 mass % to 30 mass % (Patent Literature 4), and (v) a technique for conducting a surface crosslinking reaction twice (Patent Literature 5).

As a method for modifying a surface-crosslinked water absorbent resin proposed are (i) a technique for granulating a surface-crosslinked water absorbent resin with water (Patent Literatures 6 and 17), (ii) a technique for granulating a heated water absorbent resin with an aqueous liquid when cooling the heated water absorbent resin (Patent Literature 7), (iii) a technique for improving an anti-damage property by adding an aqueous liquid after a heat treatment so as to adjust moisture content to 10% to 20% (Patent Literature 8), (iv) a technique for improving an anti-damage property by adjusting moisture content of a product (Patent Literature 9), (v) a technique for increasing moisture content of a water absorbent resin by heating and then humidifying and blending again the water absorbent resin (Patent Literature 10), (vi) a technique for adding a polyvalent metal salt aqueous solution after surface crosslinking (Patent Literatures 11 and 12), (vii) a technique for adding an alkanolamine aqueous solution after surface crosslinking (Patent Literature 13), (viii) a technique for adding a water dispersion liquid of metallic soap after surface crosslinking (Patent Literature 18), (ix) a technique for granulating a surface-crosslinked water absorbent resin with water vapor (Patent Literature 20), and (x) a technique for reducing a residual monomer by carrying out heating to not lower than 60° C. in the presence of water vapor (Patent Literature 24).

As a method for improving a drying step after polymerization proposed is a technique for drying by heating at 80° C. to 250° C. with a gas whose dew point falls within a range from 50° C. to 100° C. so as to reduce a residual monomer (Patent Literature 25).

On the other hand, a water absorbent resin produced by means of the above-described surface-crosslinking technique etc. is sometimes mechanically damaged in a transportation step or in a filling step, or, for example, when being processed by a user into absorbent articles such as disposable diapers. Specifically, for example, a surface-crosslinked layer of or a particle itself of the water absorbent resin is destroyed. This causes generation of dust and/or deterioration in physical properties of the water absorbent resin. As a method for producing a water absorbent resin which is not damaged when being transported proposed is a method for producing a water absorbent resin with a gas having a low dew point in a range from −5° C. to −100° C. (Patent Literature 23).

The above phenomenon is a problem related to an anti-damage property of a water absorbent resin. As a method for addressing the problem proposed is a technique for adding water or an aqueous solution to a surface-crosslinked water absorbent resin (Patent Literatures 9 through 13). As a technique for preventing dust of a water absorbent resin proposed is a technique for adding a dust inhibiting agent (Patent Literatures 14 through 16).

Conventional water absorbent resins produced by means of these techniques do not attain all of (i) a high water absorption capacity (CRC), (ii) a high water absorption capacity under load (AAP), (iii) reducing fine powder (which passes through a sieve having a mesh size of 150 μm or 106 μm), and (iv) suppressing quantity of fine powder to be generated due to damage of the water absorbent resins.

CITATION LIST

Patent Literatures

Patent Literature 1
Specification of United States Patent Application Publication No. 2011/0319518
Patent Literature 2
Specification of U.S. Pat. No. 6,720,389
Patent Literature 3
Specification of United States Patent Application Publication No. 2012/0172536
Patent Literature 4
Japanese Patent Application Publication, Tokukaihei, No. 03-195705 (1991)
Patent Literature 5
Specification of U.S. Pat. No. 5,672,633
Patent Literature 6
Specification of U.S. Pat. No. 5,096,944
Patent Literature 7
Specification of U.S. Pat. No. 7,378,453
Patent Literature 8
Japanese Patent Application Publication, Tokukaihei, No. 09-124879 (1997)
Patent Literature 9
Specification of United States Patent Application Publication No. 2009/0186542
Patent Literature 10
Specification of United States Patent Application Publication No. 2010/0323885
Patent Literature 11
Specification of U.S. Pat. No. 7,507,475
Patent Literature 12
Specification of U.S. Pat. No. 6,323,252
Patent Literature 13
Specification of U.S. Pat. No. 6,414,214
Patent Literature 14
Specification of U.S. Pat. No. 5,728,742
Patent Literature 15
Specification of U.S. Pat. No. 5,994,440
Patent Literature 16
Specification of U.S. Pat. No. 6,090,875
Patent Literature 17
Specification of U.S. Pat. No. 7,473,470
Patent Literature 18
Specification of United States Patent Application Publication No. 2012/0184670
Patent Literature 19
Specification of U.S. Pat. No. 8,546,492
Patent Literature 20
Specification of United States Patent Application Publication No. 2011/0237739
Patent Literature 21
International Application No. PCT/JP2013/072206 (International Filing Date: Aug. 20, 2013)
Patent Literature 22
International Application No. PCT/JP2013/072207 (International Filing Date: Aug. 20, 2013)
Patent Literature 23
Specification of U.S. Pat. No. 8,410,223
Patent Literature 24
Specification of U.S. Pat. No. 8,299,207
Patent Literature 25
Specification of U.S. Pat. No. 4,920,202

SUMMARY OF INVENTION

Technical Problem

As has been described, many surface-crosslinking techniques, etc. have been proposed so far for the purpose of improving physical properties of a water absorbent resin. Particularly, methods for surface-crosslinking a water absorbent resin (Patent Literatures 1 through 5) and methods for improving moisture content after surface crosslinking (Patent Literatures 8 through 11) have been proposed so as to obtain a water absorbent resin which less generates fine powder and has an excellent anti-damage property in accordance with functional sophistication of disposable diapers.

However, the methods of Patent Literatures 1 through 7 cannot carry out a stable and continuous production because a water absorbent resin adheres to an inner wall etc. of a mixer, a reactor or a cooling apparatus, thereby sometimes deteriorating productivity and physical properties. The methods bring about some effect when they are used in a small-scale production in a laboratory etc. However, the methods sometimes do not bring about a sufficient effect when they are used in a large-scale production in a plant (which produces, for example, at least 1 ton per hour).

The methods of Patent Literatures 8 through 13 use an aqueous solution where an inorganic compound, polyvalent metal salt or alkanolamine is dissolved, in order to improve an anti-damage property (also referred to as impact resistance). This increases cost merely for the purpose of reducing quantity of fine powder of a water absorbent resin and improving the anti-damage property.

The techniques of using a dust inhibiting agent so as to prevent dust, disclosed in Patent Literatures 14 through 16, do not improve physical properties of a water absorbent resin. The techniques not only increase cost but also excessively reduce surface tension of the water absorbent resin depending on kinds of the dust inhibiting agent, and therefore sometimes increases quantity of a liquid which has been absorbed by a disposable diaper but returns to be unabsorbed again.

The present invention was made in view of the problems, and an object of the present invention is to provide (i) a polyacrylic acid (salt)-based water absorbent resin which less generates fine powder and has an excellent anti-damage property even in a case where the polyacrylic acid (salt)-based water absorbent resin is produced on a large scale and (ii) a method for producing the polyacrylic acid (salt)-based water absorbent resin.

Solution to Problem

In order to attain the object, the inventors of the present invention (i) diligently studied a method for producing a water absorbent resin, (ii) consequently found that it was possible to reduce quantity of fine powder of the water absorbent resin and to improve an anti-damage property by controlling an atmospheric dew point and a temperature of the water absorbent resin in a case where an aqueous liquid is added during and/or after reaction, and (iii) completed the present invention. The inventors of the present invention particularly (i) found that a water absorbent resin having a high water absorption capacity (CRC), a high water absorption capacity under load (AAP), and a predetermined moisture content, i.e., a moisture content in a range from 5% to 20% reduced quantity of fine powder of the water absorbent resin and improved an anti-damage property, and (ii) completed the present invention.

That is, in order to attain the object, as a method of the present invention for producing a polyacrylic acid (salt)-based water absorbent resin particle provided is a method for producing a polyacrylic acid (salt)-based water absorbent resin particle including the steps of: (a) adding a surface crosslinking agent solution to water absorbent resin powder to obtain a mixture; (b) reacting the mixture; and, thereafter (c) adding an aqueous liquid to at least one selected from the group consisting of (i) the water absorbent resin powder during the step (b) and (ii) the water absorbent resin powder after the step (b), an atmospheric dew point being not lower than 20° C. in the step (c), and a temperature of the water absorbent resin powder being higher than the atmospheric dew point in the step (c).

Further, in order to attain the object, as a polyacrylic acid (salt)-based water absorbent resin of the present invention provided is a polyacrylic acid (salt)-based water absorbent resin having (i) a moisture content in a range from 5 wt % to 20 wt %, (ii) a water absorption capacity without load CRC (ERT 441.2-02) in a range from 30 to 45 (g/g), (iii) a water absorption capacity under load AAP (ERT 442.2-02) in a range from 30 to 40 (g/g), and (iv) a total of the CRC and the AAP of not less than 65 (g/g).

Advantageous Effects of Invention

According to the method of the present invention, it is possible to simply and easily, and uniformly add an aqueous liquid to a water absorbent resin. This makes it possible to simplify a process and to prevent physical properties from being deteriorated due to process damage. This further makes it possible to stably produce a water absorbent resin having a high moisture content.

DESCRIPTION OF EMBODIMENTS

The following description will discuss in detail a method of the present invention for producing a polyacrylic acid (salt)-based water absorbent resin particle. The scope of the present invention, however, is not limited to this description. Besides examples below, the present invention can also be modified as appropriate so as not to fail to attain the object of the present invention, and can be put into practice. Specifically, the present invention is not limited to the description of the embodiments below, and can therefore be modified by a skilled person in the art within the scope of the claims. An embodiment derived from a proper combination of technical means disclosed in different embodiments is encompassed in the technical scope of the present invention.

[1] Definition of Terms (1-1) "Water Absorbent Resin"

"Water absorbent resin" of the present invention means a water-swellable water-insoluble polymer gelatinizer having (i) water swellability represented by a CRC (water absorption capacity without load) of not less than 5 [g/g] and (ii) water insolubility represented by an Ext (water soluble component) of not more than 50 wt %.

The water absorbent resin can be designed as appropriate according to its use and/or purposes, and is not limited to a particular structure. It is, however, preferable that the water absorbent resin be a hydrophilic crosslinked polymer in which an unsaturated monomer having a carboxyl group is crosslinked and polymerized. The water absorbent resin is neither limited to being totally a polymer (100 wt %). As long as the above physical properties (CRC and Ext) are met, the water absorbent resin may be a water absorbent resin composition containing an additive etc. Note that, in this specification, the water absorbent resin composition containing the additive etc., an intermediate obtained in an intermediate step (e.g., a mixture obtained in a mixing step or a reactant obtained in a reaction step), and an end product are generically called "water absorbent resin", unless otherwise specified.

In a case where the water absorbent resin is the water absorbent resin composition, quantity of the water absorbent resin (polyacrylic acid (salt)-based water absorbent resin) contained in the water absorbent resin composition is preferably in a range from 70 wt % to 99.9 wt %, more preferably in a range from 75 wt % to 99 wt %, still more preferably in a range from 80 wt % to 97 wt %, and particularly preferably in a range from 80 wt % to 95 wt %.

In terms of water absorbing speed and impact resistance, the water absorbent resin composition preferably contains water as a component other than the water absorbent resin. The water absorbent resin composition further contains an additive (later described), if necessary.

(1-2) "Polyacrylic Acid (Salt)"

"Polyacrylic acid (salt)" of the present invention means a polymer (i) which may contain a graft component as appropriate and (ii) whose main component is acrylic acid and/or its salt (hereinafter referred to as "acrylic acid (salt)") as its repeating unit.

The term "main component" means that quantity of the acrylic acid (salt) to be contained (used) relative to the total quantity of monomer (including no crosslinking agent) to be polymerized is typically in a range from 50 mol % to 100 mol %, preferably in a range from 70 mol % to 100 mol %, more preferably in a range from 90 mol % to 100 mol %, and still more preferably substantially 100 mol %. The polyacrylic acid may be a polyacrylic acid (salt) obtained by saponifying polyacrylonitrile or polyacrylamide.

In a case where the polyacrylic acid salt is a polymer, the polyacrylic acid salt essentially contains a water-soluble salt, preferably a monovalent salt, more preferably an alkali metal salt or ammonium salt, still more preferably an alkali metal salt, and particularly preferably a sodium salt.

(1-3) "EDANA" and "ERT"

"EDANA" stands for European Disposables and Nonwovens Associations. "ERT" stands for EDANA Recommended Test Methods, which is a water absorbent resin measuring method adopted as the European standard.

In the present invention, unless otherwise specified, physical properties of a water absorbent resin are measured according to the ERT master copy (publicly-known literature: 2002 revised version).

(a) "CRC" (ERT 441.2-02)

"CRC" stands for Centrifuge Retention Capacity, and means water absorption capacity without load (hereinafter, may be referred to as "water absorption capacity").

Specifically, "CRC" is water absorption capacity (unit; g/g) measured after allowing 0.2 g of a water absorbent resin wrapped in unwoven cloth to freely swell with a 0.9 wt % sodium chloride aqueous solution in a largely excess amount for 30 minutes and then draining the water absorbent resin with a centrifugal apparatus (250 G).

(b) "AAP" (ERT 442.2-02)

"AAP" stands for Absorption Against Pressure, and means water absorption capacity under load.

Specifically, "AAP" is water absorption capacity (unit; g/g) measured after allowing 0.9 g of a water absorbent resin to swell with a 0.9 wt % sodium chloride aqueous solution in a largely excess amount for 1 hour under load of 2.06 kPa (0.3 psi).

(c) "Ext" (ERT 470.2-02)

"Ext" stands for Extractables, and means water soluble component.

Specifically, "Ext" is a value (unit; wt %) obtained by adding 1.0 g of a water absorbent resin to 200 ml of a 0.9 wt % sodium chloride aqueous solution, stirring at 500 rpm for 16 hours, and then measuring quantity of a dissolved polymer by means of pH titration.

(d) "Moisture Content" (ERT430.2-02)

"Moisture Content" means moisture content of a water absorbent resin.

Specifically, "Moisture Content" is a value (unit; wt %) calculated from drying loss found by drying 4.0 g of a water absorbent resin at 105° C. for 3 hours. Note that, in the present invention, 4.0 g and 105° C. were changed to 1.0 g and 180° C., respectively, and the value was found.

(e) "Residual Monomers" (ERT410.2-02)

"Residual monomers" mean quantity of monomers left in a water absorbent resin.

Specifically, "Residual Monomers" is a value (unit; ppm) found by adding 1.0 g of a water absorbent resin to 200 ml of a 0.9 wt % sodium chloride aqueous solution, stirring at 500 rpm for 1 hour, and then measuring quantity of dissolved residual monomers by means of high performance liquid chromatography (HPLC).

(f) "PSD" (ERT 420.2-02)

"PSD" stands for Particle Size Distribution, and means particle size distribution measured by sieve classification. Note that a weight average particle diameter (D50) and a particle size distribution range are measured by the same method as that for measuring "(1) Average Particle Diameter and Distribution of Particle Diameter" described in European Patent No. 0349240 and International Publication No. WO2004/069915.

(g) Other Physical Properties Defined by EDANA

"pH" (ERT400.2-02) means pH of a water absorbent resin.

"Flow Rate" (ERT450.2-02) means a flow speed of a water absorbent resin.

"Density" (ERT460.2-02) means bulk specific gravity of a water absorbent resin.

(1-4) Others

In this specification, "X to Y" which indicates a range means "not less than X and not more than Y". Unless otherwise specified, the weight unit "t (ton)" means "metric ton", and "ppm" means "ppm by weight" or "ppm by mass". Moreover, "weight" is synonymous with "mass", "part by weight" is synonymous with "part by mass", and "wt %" is synonymous with "mass %". Further, " . . . acid (salt)" means " . . . acid and/or salt thereof", and "(meth)acrylic" means "acrylic and/or methacrylic".

[2] Method for Producing Polyacrylic Acid (Salt)-Based Water Absorbent Resin (2-1) Polymerization Step This step is a step of polymerizing an acrylic acid (salt)-based monomer aqueous solution to obtain a water-containing gel-like crosslinked polymer (hereinafter referred to as "hydrogel").

(Monomer) (Including No Crosslinking Agent)

It is preferable in terms of water absorbing ability that a polyacrylic acid (salt)-based water absorbent resin produced by the method of the present invention be produced with a monomer whose main component is an acrylic acid (salt) in which at least part of an acrylic acid is neutralized.

A partially neutralized salt of the acrylic acid is not limited to a specific one but is, in terms of water absorbing ability, preferably at least one kind of monovalent salt selected from the group consisting of alkali metal salt, ammonium salt and amine salt, more preferably alkali metal salt, still more preferably at least one kind of acrylate selected from the group consisting of sodium salt, lithium salt and potassium salt, and particularly preferably sodium salt.

A monomer which has not been polymerized and/or a polymerized hydrogel can be neutralized. A neutralization ratio is preferably in a range from 10 mol % to 100 mol %, more preferably in a range from 30 mol % to 95 mol %, still more preferably in a range from 50 mol % to 90 mol %, and particularly preferably in a range from 60 mol % to 80 mol %.

The monomer (including a crosslinking agent described below) is typically polymerized in a state where the monomer is contained in an aqueous solution. A concentration (also called solid content) of the monomer contained in the aqueous solution is typically in a range from 10 wt % to 90 wt %, preferably in a range from 20 wt % to 80 wt %, still more preferably in a range from 30 wt % to 70 wt %, particularly preferably in a range from 35 wt % to 60 wt %, and most preferably in a range from 40 wt % to 55 wt %.

In terms of improving physical properties of a water absorbent resin to be produced, an optional component such as (i) a foaming agent, e.g., carbonate, an azo compound or air bubble, (ii) an additive, e.g., a surfactant or a chelating agent, (iii) starch, (iv) a water-soluble or water-absorbent resin, e.g., polyvinyl alcohol or polyacrylic acid (salt) can be add to (i) an aqueous solution containing a monomer whose main component is an acrylic acid (salt), (ii) a polymerized hydrogel, or (iii) a water absorbent resin of a dried polymer, a pulverized polymer or the like.

Quantity of the optional component to be added relative to a monomer is preferably in a range from 0 wt % to 5 wt %, and more preferably in a range from 0 wt % to 1 wt %. Quantity of the water-soluble or water-absorbent resin to be added relative to a monomer is preferably in a range from 0 wt % to 50 wt %, more preferably in a range from 0 wt % to 20 wt %, still more preferably in a range from 0 wt % to 10 wt %, and particularly preferably in a range from 0 wt % to 3 wt %.

In the present invention, in a case where the optional component is added within the above range relative to the monomer whose main component is the acrylic acid (salt), a hydrophilic or hydrophobic unsaturated monomer can be used in addition to the acrylic acid (salt).

The hydrophilic or hydrophobic unsaturated monomer is not limited to a specific one. Examples of the hydrophilic or hydrophobic unsaturated monomer include methacrylic acid, maleic acid (maleic anhydride), 2-(meth)acrylamide-2-methyl propanesulfonic acid, (meth)acryloxyalkanesulfonic acid, N-vinyl-2-pyrolidone, N-vinylacetamide, (meth)acrylamide, N-isopropyl(meth)acrylamide, N,N-dimethyl (meth)acrylamide, 2-hydroxyethyl(meth)acrylate, methoxypolyethyleneglycol(meth)acrylate, polyethyleneglycol (meth)acrylate, stearylacrylate, and salts thereof, etc.

In terms of the physical properties of the water absorbent resin to be produced, the hydrophilic or hydrophobic unsaturated monomer to be used relative to the total monomer is preferably in a range from 0 wt % to 50 wt %, and more preferably in a range from 0 wt % to 20 wt %.

(Crosslinking Agent (Internal Crosslinking Agent))

In the present invention, it is preferable in terms of a water absorbing property to use a crosslinking agent (internal crosslinking agent). The crosslinking agent (internal crosslinking agent) is not limited to a specific one. Examples of the crosslinking agent include (i) a polymerizable crosslinking agent which is polymerizable with an acrylic acid, (ii) a reactive crosslinking agent which is reactive with a carboxyl group, and (iii) a crosslinking agent which is polymerizable with an acrylic acid and reactive with a carboxyl group.

Examples of the polymerizable crosslinking agent include compounds each having at least two polymerizable double bonds in a molecule, such as N,N'-methylene bis(meth)acrylamide, (poly)ethylene glycol di(meth)acrylate, (polyoxyethylene)trimethylolpropane tri(meth)acrylate, and poly(meth)allyloxy alkane.

Examples of the reactive crosslinking agent include (i) covalent bonding crosslinking agents such as polyglycidyl ether (e.g., ethylene glycol diglycidyl ether) and polyvalent alcohol (e.g., propanediol, glycerine, and sorbitol), and (ii) an ionic bonding crosslinking agent such as a polyvalent metal compound of aluminum salt etc. Among these, in terms of the water absorbing property, the crosslinking agent is preferably the polymerizable crosslinking agent which is polymerizable with acrylic acid, particularly preferably an acrylate-based, allyl-based or acrylamide-based polymerizable crosslinking agent. One or more kind(s) of these internal crosslinking agents can be used.

In terms of physical properties, quantity of the internal crosslinking agent to be used relative to the monomer including no crosslinking agent is preferably in a range from 0.001 mol % to 5 mol %, more preferably in a range from 0.005 mol % to 2 mol %, still more preferably in a range from 0.01 mol % to 1 mol %, and particularly preferably in a range from 0.03 mol % to 0.5 mol %.

(Polymerization Initiator)

A polymerization initiator used in the present invention is selected as appropriate according to polymerization scheme. Examples of the polymerization initiator include a photolytic-type polymerization initiator, a pyrolysis-type polymerization initiator, a redox-type polymerization initiator, and the like. Quantity of the polymerization initiator to be used relative to the monomer is preferably in a range from 0.0001 mol % to 1 mol %, and more preferably in a range from 0.001 mol % to 0.5 mol %.

Examples of the photolytic-type polymerization initiator include a benzoin derivative, a benzyl derivative, an acetophenone derivative, a benzophenone derivative, an azo compound, and the like. Examples of the pyrolysis-type polymerization initiator include (i) persulfate such as sodium persulfate, potassium persulfate or ammonium persulfate, (ii) peroxide such as hydrogen peroxide, t-butyl peroxide or methyl-ethyl-ketone peroxide, (iii) an azo compound such as 2,2'-azobis(2-amidino propane) dihydrochloride or 2,2'-azobis[2-(2-imidazoline 2-yl) propane] dihydrochloride, and the like.

An example of the redox-type polymerization initiator is a system in which a reducible compound such as L-ascorbic acid or sodium hydrogensulfite is used in combination with the persulfate or the peroxide. It is one preferable aspect to use the photolytic-type polymerization initiator and the pyrolysis-type polymerization initiator in combination.

(Polymerization Method)

In terms of performance and polymerization control, spraying polymerization, droplet polymerization, aqueous polymerization, or reverse-phase suspension polymerization is employed as a polymerization method of the present invention. Among these, the aqueous polymerization is preferably employed. Continuous aqueous polymerization is still more preferably employed. A water absorbent resin obtained by the aqueous polymerization or the continuous aqueous polymerization has a non-uniformly pulverized shape. The water absorbent resin having the non-uniformly pulverized shape is likely to generate fine powder in a subsequent pulverization step etc. In the present invention, however, it is possible to reduce quantity of fine powder by adding an aqueous liquid in a surface crosslinking step.

Preferable embodiments of the continuous aqueous polymerization include, for example, continuous kneader polymerization (disclosed in U.S. Pat. No. 6,987,151 and No. 6710141, etc.) and continuous belt polymerization (disclosed in U.S. Pat. No. 4,893,999 and No. 6241928, United States Patent Application Publication No. 2005/215734, etc.). These kinds of continuous aqueous polymerization can produce a water absorbent resin with high productivity.

According to the present invention, even by such a high-concentration or high-temperature polymerization, it is possible to produce a water absorbent resin whose monomer has an excellent stability and which has a high degree of whiteness. The present invention more remarkably brings about an effect under such a condition. The high-temperature polymerization starting at a high temperature is disclosed in U.S. Pat. No. 6,906,159 and No. 7091253, etc. According to the method of the present invention, a monomer which has not been polymerized has an excellent stability. It is therefore easy to perform industrial-scale production.

These kinds of polymerization can be carried out under air atmosphere. It is, however, preferable in terms of coloring improvement that these kinds of polymerization be carried out under inert gas atmosphere such as nitrogen or argon (with, for example, an oxygen concentration of not more than 1% by volume). It is also preferable that these kinds of polymerization be carried out after oxygen (for example, less than 1 [mg/L] of oxygen) dissolved in a monomer or in a monomer-containing solution is sufficiently substituted for inert gas.

(2-2) Gel-Crushing Step

This step is a step of crushing, with a gel crusher such as a kneader, a meat chopper or a cutter mill, a hydrogel obtained in the polymerization step to obtain a hydrogel in the form of a particle (hereinafter referred to as "particulate hydrogel"). Note that, in a case where kneader polymerization is carried out in the polymerization step, the polymerization step and the gel-crushing step can be carried out simultaneously. Note also that the hydrogel may be supplied to a drying step without the gel-crushing step. If necessary, a step of maturing the hydrogel or the particulate hydrogel (particularly, a step of promoting polymerization etc. by means of heating or heat-retention) can be carried out before or after the gel-crushing step.

In this step, water, polyvalent alcohol, a mixture liquid of water and polyvalent alcohol, a polyvalent metal (salt) aqueous solution, water vapor thereof or the like can be added to the hydrogel, in terms of (i) improvement of crushability of the hydrogel and (ii) improvement of physical properties of the hydrogel.

In the present invention, it is preferable that a gel crushing time (a time from an end of polymerization to a start of drying) be short, in terms of (i) reduction in residual monomer, (ii) prevention of deterioration in gel (improvement of an anti-urine property), and (iii) prevention of yellowing. Specifically, the gel crushing time is preferably not longer than 1 hour, more preferably not longer than 0.5 hour, and still more preferably not longer than 0.1 hour. A temperature of the hydrogel which is being gel-crushed is controlled (retained or heated) to preferably 40° C. to 95° C., more preferably 50° C. to 80° C., and still more preferably 60° C. to 70° C.

The crushed particulate hydrogel has a resin solid content preferably in a range from 10 wt % to 90 wt %, more preferably in a range from 20 wt % to 80 wt %, still more preferably in a range from 30 wt % to 70 wt %, and particularly preferably in a range from 35 wt % to 60 wt %. The particulate hydrogel has a weight average particle diameter (D50) (defined by sieve classification) preferably in a range from 0.2 mm to 10 mm, more preferably in a range from 0.3 mm to 5 mm, and still more preferably in a range from 0.5 mm to 3 mm. A ratio of a particulate hydrogel whose particle diameter is not less than 5 mm to the whole particulate hydrogel is preferably in a range from 0 wt % to 10 wt %, and more preferably in a range from 0 wt % to 5 wt %. Note that a particle diameter of a particulate hydrogel is measured in conformity to a wet classification method disclosed in paragraph [0091] of Japanese Patent Application Publication, Tokukai, No. 2000-63527.

(2-3) Drying Step

This step is a step of drying, to a desired degree, a hydrogel and/or a particulate hydrogel obtained in the polymerization step and/or the gel-crushing step to obtain a dried polymer. Note that a resin solid content of the dried polymer can be found from drying loss (change in weight of 1 g of a sample heated at 180° C. for 3 hours). The resin solid content relative to the dried polymer is preferably not less than 80 wt %, more preferably in a range from 85 wt % to 99 wt %, still more preferably in a range from 90 wt % to 98 wt %, and particularly preferably in a range from 92 wt % to 97 wt %. Note here that both a high AAP and a high CRC will not probably be attained by the technique of Patent Literature 4 for further adding (5 wt % to 20 wt % of) an aqueous liquid while heating a water absorbent resin whose moisture content is in a range from 10 mass % to 30 mass %.

A drying method of the present invention is not particularly limited provided that the drying method dries the hydrogel and/or the particulate hydrogel to obtain the dried polymer having the resin solid content in the above range. The drying method can be selected as appropriate from thermal drying, hot-air drying, drying under reduced pressure, infrared drying, microwave drying, drying with a drum dryer, drying by azeotropic dehydration with a hydrophobic organic solvent, high-humidity drying with high-temperature water vapor, etc. Among these drying methods, the hot-air drying is preferably employed. More preferably employed is hot-air drying with a gas whose dew point is in a range from 0° C. to 100° C. Still more preferably employed is hot-air drying with a gas whose dew point is in a range from 20° C. to 90° C.

In terms of a water absorbing property or color tone, a drying temperature is controlled (heated) to preferably a range from 100° C. to 300° C., and more preferably a range from 150° C. to 250° C. Particularly, in terms of attaining both physical properties of and degree of whiteness of a water absorbent resin to be produced, it is preferable that the drying temperature be in a range from 165° C. to 230° C., and a drying time be not longer than 50 minutes. It is more preferable that the drying time be in a range from 20 to 40 minutes. Note that, in a case where hot-air drying is employed, a temperature of hot air is regarded as a drying temperature. It is not preferable to dry a hydrogel and/or a particulate hydrogel at a drying temperature which is not in the above range and/or for a drying time which is not in the above range. This is because such drying probably reduces a water absorption capacity without load (CRC) of a water absorbent resin, increases a water soluble component of the water absorbent resin, and/or decreases degree of whiteness of the water absorbent resin.

(2-4) Pulverization Step

This step is a step of pulverizing a dried polymer obtained in the drying step to obtain a pulverized polymer (water absorbent resin powder). Note that, in a case where a hydrogel obtained in the polymerization step is in the form of a particle (for example, in a case where spraying polymerization, droplet polymerization or reverse-phase suspension polymerization is carried out in the polymerization step), the pulverization step is not sometimes carried out after the drying step.

No particular limitation is placed on a pulverizing apparatus used in the pulverization step. Examples of the pulverizing apparatus include a roll mill, a hammer mill, a roll granulator, a Jaw crusher, a Jai Rectory crusher, a cone crusher, a roll crusher, a cutter mill, and the like. Among these apparatuses, it is preferable to use a multiple-stage roll mill or roll granulator in terms of particle size control.

(2-5) Classification Step

This step is a step of classifying a pulverized polymer obtained through the above-described steps (the polymerization step, the gel-crushing step, the drying step, and the pulverization step) to obtain water absorbent resin powder.

A classification step of the present invention is not particularly limited. An example of the classification method is sieve classification with a JIS standard sieve (JIS Z8801-1 (2000)), or the like. Note that a particle size of the water absorbent resin powder can also be adjusted as appropriate in the polymerization step (particularly, a reverse-phase suspension polymerization step or a spraying droplet polymerization step) or in other step (e.g., a granulation step, a fine powder recycling step, or the like) in addition to the classification step.

The classification step needs only to be carried out at least once (at least at one place) during a process for producing a polyacrylic acid (salt)-based water absorbent resin particle. It is preferable to carry out the classification step at least twice (at least at two places) during the process. It is more preferable to carry out the classification step at least once (at least at one place) before and/or after the surface crosslinking step. The classification step can be carried out three to six times, if necessary.

The water absorbent resin powder obtained in the classification step has a particle size, i.e., a weight average particle diameter (D50) preferably in a range from 200 μm to 600 μm, more preferably in a range from 200 μm to 550 μm, still more preferably in a range from 250 μm to 500 μm, and particularly preferably in a range from 300 μm to 450 μm. The water absorbent resin powder contains a particle whose diameter is less than 150 μm preferably in a range from 0 wt % to 10 wt %, more preferably 0 wt % to 5 wt %, and still more preferably 0 wt % to 1 wt %. The water absorbent resin powder contains a particle whose particle diameter is not less than 850 μm preferably in a range from 0 wt % to 5 wt %, more preferably in a range from 0 wt % to 3 wt %, and still more preferably in a range from 0 wt % to 1 wt %. Logarithmic standard deviation (σ) of particle size distribution is preferably in a range from 0.20 to 0.50, more preferably in a range from 0.25 to 0.40, and still more preferably in a range from 0.27 to 0.35. Note that the particle size is measured with a standard sieve in conformity to a measurement method disclosed in International Publication No. WO2004/69915 or EDANA ERT420.2-02.

The above-described particle size is applied to not only water absorbent resin powder which has not been surface-crosslinked but also a surface-crosslinked water absorbent resin particle and a polyacrylic acid (salt)-based water absorbent resin particle as an end product. It is therefore necessary to carry out surface crosslinking so as to maintain the particle size in the above range.

(2-6) Surface Crosslinking Step

This step is a step of causing part of a surface layer of water absorbent resin powder obtained through the above steps (part several tens of micrometers deep from a surface of the water absorbent resin powder) to have a high crosslinking density. The surface crosslinking step is made up of the following steps 1) through 5).

Examples of surface crosslinking applicable to the present invention include (i) radical cross-linkage of a surface of water absorbent resin powder with persulfate, a photopolymerization initiator, etc. (see, for example, pamphlet of International Publication No. WO2006/062258, and U.S. Pat. No. 4,910,250), (ii) polymerization surface-crosslinking which carries out polymerization with an added monomer (see, for example, U.S. Pat. No. 7,201,941, pamphlet of International Publication No. WO2009/048160A, and pamphlet of International Publication No. WO2006/062253), (iii) coating crosslinking which adds a water-soluble polymer and a surface crosslinking agent (see, for example, claims 2 and 4 of U.S. Pat. No. 4,727,097), and the like, in addition to (iv) the methods disclosed in Patent Literatures 1 through 5, 8, 21 and 22, etc. and (v) crosslinking with a polyfunctional surface crosslinking agent (later described). Various surface crosslinking agent solutions are used in accordance with the techniques. Note here that, in a case where surface crosslinking is carried out with persulfate, a photopolymerization initiator, etc., the persulfate, the photopolymerization initiator, etc. serves as a surface crosslinking agent. Note also that, in a case where surface crosslinking is carried out with a monomer etc., the monomer etc. serves as a surface crosslinking agent.

The following description will mainly discuss surface crosslinking with a polyfunctional surface crosslinking agent, which typifies these kinds of surface crosslinking (surface crosslinking agent solutions). However, the present invention is not particularly limited to the description.

1) Mixing Step

This step is a step of (i) adding a surface crosslinking agent (or a liquid solution or dispersion liquid thereof) to water absorbent resin powder obtained through the above-described (2-1) Polymerization Step through (2-5) Classification Step and (ii) mixing them to obtain a water absorbent resin mixture (hereinafter referred to simply as "mixture", also in Examples).

(Surface Crosslinking Agent)

A surface crosslinking agent usable in the present invention is not particularly limited. Various organic or inorganic surface crosslinking agents can be used. Among these surface crosslinking agents, an organic surface crosslinking agent which reacts with a carboxyl group to form a covalent bond is preferably employed in terms of (i) physical properties of a water absorbent resin and (ii) ease of use of a surface crosslinking agent.

Specifically, at least one kind of surface crosslinking agent described in columns 9 and 10 of U.S. Pat. No. 7,183,456 can be used. The total quantity of the at least one kind of surface crosslinking agent to be used relative to 100 parts by weight of the water absorbent resin powder is preferably in a range from 0.01 to 10 part(s) by weight, and more preferably in a range from 0.01 to 5 part(s) by weight.

Further specific examples of a preferable surface crosslinking agent usable in the present invention include an epoxy compound, a polyvalent alcohol compound, a polyvalent amine compound, a haloepoxy compound, an oxazolidinone compound, an oxetane compound, and an alkylene carbonate compound.

It is preferable to add, to the water absorbent resin powder, the surface crosslinking agent which is dissolving in water that is a solvent. Quantity of the water to be used relative to 100 parts by weight of the water absorbent resin powder is preferably in a range from 0.1 to 20 part(s) by weight, and more preferably in a range from 0.5 to 10 part(s) by weight. If necessary, a hydrophilic organic solvent can be further used as the solvent. Quantity of the hydrophilic organic solvent to be used relative to 100 parts by weight of the water absorbent resin powder is preferably not more than 10 parts by weight, and more preferably not more than 5 parts by weight.

(Adding and Mixing Method)

A method for adding and mixing the surface crosslinking agent is not particularly limited in the present invention. On the other hand, (i) a surface crosslinking agent, and water as a solvent or a hydrophilic organic solvent or (ii) a mixture thereof which is prepared in advance are/is preferably sprayed or dropped, and more preferably sprayed over the water absorbent resin powder, and then mixed.

A mixing apparatus used to mix the surface crosslinking agent with the water absorbent resin powder is not particularly limited. Preferably used is a high-speed stirring-type mixing apparatus. More preferably used is a high-speed stirring-type continuous mixing apparatus. Still more preferably used is a transverse or longitudinal-type and high-speed stirring-type continuous mixing apparatus. More specific examples of the mixing apparatus include a SHUGI mixer (manufactured by Powrex Corporation), a Turbulizer (manufactured by HOSOKAWA MICRON CORPORATION), a Loedige mixer (manufactured by Gebrüder Lödige Maschinenbau GmbH), and the like.

Of operation conditions of the mixing step of the present invention, (i) the number of revolutions is preferably in a range from 100 rpm to 10000 rpm, and more preferably in a range from 300 rpm to 2000 rpm, and (ii) a retention time is preferably within 180 seconds, more preferably in a range from 0.1 to 60 second(s), and still more preferably in a range from 1 to 30 second(s).

A temperature of the water absorbent resin powder to be supplied to the mixing step is preferably not lower than 30° C., more preferably not lower than 40° C., and still more preferably not lower than 50° C. An upper limit of the temperature is preferably not higher than 100° C., and more preferably not higher than 95° C. By setting the temperature of the water absorbent resin powder to the above range, it is possible to prevent the physical properties of the water absorbent resin from deteriorating.

2) Reaction Step

This step is a step of causing a crosslinking reaction of a surface of water absorbent resin powder by heating a mixture obtained in the mixing step and/or irradiating the mixture with an active energy ray to obtain a reacted water absorbent resin (hereinafter referred to simply as "reactant", also in Examples). The crosslinking reaction can be found as appropriate from, for example, (i) decrease in free swelling capacity (e.g., CRC or FSC) due to crosslinking, (ii) reduction in quantity of an added surface crosslinking agent, or (iii) a crosslinking structure of a surface of the reacted water absorbent resin (e.g., formation of an ester structure).

An apparatus used in the reaction step may be identical in structure to that used in the mixing step. The apparatus used in the reaction step is preferably different in structure from that used in the mixing step. If necessary, a storage step and/or a stirring step which do not cause a reaction of the mixture may be carried out between the mixing step and the reaction step so as to infiltrate or disperse the surface crosslinking agent into the water absorbent resin powder before the reaction step.

Particularly in a case where an aqueous liquid is added, the apparatus used in the reaction step preferably has an air inlet and/or an air outlet, particularly the air outlet. It is preferable that (i) a gas such as water vapor be supplied via the air inlet and (ii) the supplied gas, water vapor additionally generated in the apparatus, and like gases are exhausted via the air outlet so that a dew point is controllable. The number of each of the air inlet and the air outlet of the apparatus is not particularly limited, and may therefore be one, or two or more.

The air inlet and the air outlet may also serve as an inlet of and an outlet of water absorbent resin powder, respectively. It is more preferable that at least one of the air inlet and the air outlet do not also serve as a corresponding one of the inlet and the outlet of the water absorbent resin powder. It is still more preferable that at least one of a plurality of air inlets and at least one of a plurality of air outlets do not also serve as the inlet and the outlet of the water absorbent resin powder, respectively.

A gas exhausted from the apparatus may be discarded or may be recycled as it is in the reaction step. In a case where the gas is recycled, the gas may be optionally mixed with another gas, and, if necessary, heated or cooled, pressurized or depressurized, and/or humidified or dehumidified so that a temperature, a dew point, etc. is/are adjusted, and then reused in the reaction step or other step.

A surface crosslinking reaction caused in the reaction step includes, for example, (i) radical crosslinking of a surface of water absorbent resin powder with persulfate, a photopolymerization initiator, etc., (ii) polymerization crosslinking which carries out polymerization with an added monomer, and (iii) coating crosslinking which adds a water-soluble polymer and a surface crosslinking agent.

In the present invention preferably used is a covalent bonding surface crosslinking agent, an ionic bonding surface crosslinking agent, each of which reacts with a carboxyl group of a polyacrylic acid, or a combination of the covalent bonding surface crosslinking agent and the ionic bonding surface crosslinking agent. The surface crosslinking reaction produces a surface-crosslinked water absorbent resin.

Note that water absorbent resin powder does not necessarily react with a surface crosslinking agent at a reaction ratio of 100% provided that a reactant attains target physical properties. A highly-safe polyvalent alcohol etc. may be left on a surface of reacted water absorbent resin powder. The polyvalent alcohol added as a surface crosslinking agent and left on the surface can serve as a dust inhibiting agent and a hydrophilization agent.

In the present invention, reaction of a mixture (reaction of water absorbent resin powder with a surface crosslinking agent) may be caused at room temperature. The reaction is preferably caused by carrying out a heat treatment and/or an irradiation treatment of irradiating with an active energy ray (particularly, ultraviolet rays). Note that, in a case where an aqueous liquid (later described) is added during the reaction step, the aqueous liquid may be added during a surface crosslinking reaction or after the surface crosslinking reaction ends. The heat treatment and the irradiation treatment of irradiating with an active energy ray can be carried out in combination. It is, however, preferable to carry out the heat treatment in terms of improvement of and stability of physical properties.

The apparatus used in the reaction step is not particularly limited, and may therefore be an unstirring (still standing) apparatus. In terms of a uniform reaction, however, a stirring apparatus or a fluidization apparatus is preferably used as the apparatus used in the reaction step. An example of a heat reactor used to cause the reaction by carrying out the heat treatment is a dryer or a heating furnace which has a stirring mechanism or a fluidizing mechanism. More specific examples of the heat reactor include a rotary dryer, a disc dryer, a paddle-type dryer, a fluidized bed dryer, an air current dryer, an infrared dryer, and the like. An example of an active energy ray reactor used to cause the reaction by carrying out the irradiation treatment of irradiating with an active energy ray instead of the heat treatment is a stirring apparatus or a fluidization apparatus which has an ultraviolet ray irradiation mechanism. As a reactor particularly preferable is the paddle-type dryer (paddle dryer), in particular a paddle-type dryer having an air inlet and/or an air outlet.

The reactor may be a continuous or batch-type reactor. In terms of productivity, the continuous reactor is preferable.

A heat source of the heat reactor is not particularly limited. Preferable examples of the heat source include steam, warm water, niter, oil, etc. A heating temperature (temperature of a heat transfer surface of a jacket etc.) is preferably in a range from 60° C. to 300° C., more preferably in a range from 70° C. to 200° C., and still more preferably in a range from 80° C. to 150° C. Note that, in the present invention, reaction at a heating temperature exceeding 100° C., further exceeding 150° C. is particularly called a high-temperature heating reaction. In a case of the high-temperature heating reaction, a cooling step (later described) is preferably carried out.

(Degree of Depressurization)

In the present invention, it is preferable that the reactor be in a depressurized state. What is meant by "depressurized state" is a state where an air pressure is lower than the atmospheric pressure. A difference between the atmospheric pressure and the air pressure of the reactor is called "degree of depressurization". The air pressure of the reactor lower than the atmospheric pressure is indicated by a positive (plus) value. For example, in a case where the atmospheric pressure is standard atmospheric pressure (101.3 kPa), "degree of depressurization of 10 kPa" means that the air pressure of the reactor is 91.3 kPa.

The degree of depressurization in the reaction step of the present invention is preferably more than 0 kPa, more preferably not less than 0.01 kPa, and still more preferably not less than 0.05 kPa. An upper limit of the degree of depressurization is preferably not more than 10 kPa, more preferably not more than 8 kPa, still more preferably not more than 5 kPa, and particularly preferably not more than 2 kPa. Degree of depressurization of more than 10 kPa (excessive depressurization) is not preferable because it brings about a poor effect relative to required equipment cost. A non-depressurized state is neither preferable because the non-depressurized state causes air having a high dew point to flow from the reactor into an apparatus which carries out a step before or after the reaction step, thereby probably causing a problem such as dew condensation or adhesion of water absorbent resin powder. A preferable range of the degree of depressurization can be optionally determined within the upper and lower limits.

(Stirring Speed)

In the present invention, a stirring speed of the reactor is preferably in a range from 2 rpm to 40 rpm, and more preferably in a range from 5 rpm to 30 rpm. A stirring speed of less than 2 rpm is not preferable because of insufficient stirring. A stirring speed of more than 40 rpm is neither preferable because fine powder is easily generated.

(Tilt Angle)

A stirring shaft of the reactor may extend in a longitudinal direction or in a traverse direction. In a case of a continuous reactor having a stirring shaft that extends in a traverse direction, the stirring shaft tilts downward, relative to a horizontal direction in which a tilt angle of the stirring shaft is 0°, from an inlet of water absorbent resin powder toward an outlet of the water absorbent resin powder at a tilt angle preferably in a range from 0.1° to 10°, more preferably in a range from 0.5° to 5°, and still more preferably in a range from 1° to 4°. The tilt angle in the above range is preferable because an obtained water absorbent resin improves its physical properties.

(Average Retention Time)

In the present invention, an average retention time (reaction time) in the reactor is determined as appropriate according to a target crosslinking density etc., and is not particularly limited. The average retention time is preferably in a range from 3 to 180 minutes, more preferably in a range from 5 to 120 minutes, and still more preferably in a range from 10 to 60 minutes. An average retention time of less than 3 minutes is not preferable because of insufficient reaction (insufficient surface crosslinking reaction). An average retention time of more than 180 minutes is neither preferable because water absorbing ability probably deteriorates.

In a case of a continuous reactor, "average retention time" according to the present invention is determined depending on various factors such as an effective volume of the continuous reactor, quantity of a mixture to be supplied, a tilt angle, a stirring speed, the shape of a stirring blade, bulk specific gravity of the mixture, kinds of surface crosslinking agent, and the height of an exhaust dam with which an outlet of the continuous reactor is provided.

3) Cooling Step (Optional)

This step is an optional step, if necessary, carried out after the reaction step (particularly, the reaction step which carries out a heat treatment, further the reaction step which carries out a high-temperature heat treatment) for the purpose of, for example, stopping a surface crosslinking reaction and/or transporting to a step following the reaction step.

In the present invention, it is preferable that the cooling step be carried out in a short time after the reaction step (particularly, a heat reaction step). A reactant exhausted from the reactor is put into a cooling apparatus which carries out the cooling step preferably within a range of more than 0 second and not more than 3 minutes, more preferably within 2 minutes, still more preferably within 1 minute, and particularly preferably within 0.5 minute. The time (time of putting the reactant into the cooling apparatus) can be controlled depending on, for example, layout of apparatuses (direct connection of the reactor with the cooling apparatus, or arrangement of the reactor and the cooling apparatus via a short distance such as a transport distance of not longer than 10 meters).

The cooling apparatus used in the cooling step is not particularly limited. A preferable example of the cooling apparatus is a stirring apparatus or a fluidization apparatus which has a cooling function of cooling the reactant via a heat transfer surface, with air current, etc.

For example, an apparatus having the same structure as that of a paddle-type dryer that is a reactor preferably used in the reaction step can be used (the size of the apparatus is changed as appropriate). In this case, a heat medium of the reactor is replaced with a coolant so that the reactor is used as the cooling apparatus. Note that, in the present invention, for convenience, the paddle-type dryer used as the cooling apparatus is called a paddle cooler so as to be clearly differentiated from the reactor used in the reaction step. Operation conditions (e.g., degree of depressurization, stirring speed, tilt angle, and average retention time) of the paddle cooler fall within respective ranges identical to those of operation conditions of the reactor used in the reaction step.

The coolant of the cooling apparatus is not particularly limited, but is preferably water, warm water, an antifreezing liquid or the like. A cooling temperature (temperature of a heat transfer surface of a jacket etc.) is preferably in a range from 0° C. to 100°, more preferably in a range from 20° C. to 90°, and still more preferably in a range from 40° C. to 80°.

(2-7) Aqueous Liquid Adding Step

This step is a step of adding an aqueous liquid to a mixture and/or a reactant which contain(s) water absorbent resin powder during the reaction step and/or during a step (particularly, the cooling step) after the reaction step. Note that the mixture and/or the reactant are/is sometimes hereinafter generically called "water absorbent resin powder".

That is, in order to attain the object, as a method of the present invention for producing a water absorbent resin particle provided is a method for producing a polyacrylic acid (salt)-based water absorbent resin particle, including the steps of: (a) adding a surface crosslinking agent solution to water absorbent resin powder to obtain a mixture; (b) reacting the mixture; and thereafter (c) adding an aqueous liquid to the water absorbent resin powder during and/or after the step (b), an atmospheric dew point being not lower than 20° C. in the step (c), and a temperature of the water absorbent resin powder being higher than the atmospheric dew point in the step (c).

The aqueous liquid adding step needs only to be carried out in a state where the atmospheric dew point and the temperature of the water absorbent resin powder meet predetermined conditions. The aqueous liquid adding step may be carried out (i) during the reaction step, the cooling step after the reaction step, or a step after the cooling step or (ii) as an independent step.

It is preferable that an apparatus used in the aqueous liquid adding step have a mixing function. As the apparatus preferably used is an apparatus identical in structure to that used in the mixing step of the surface crosslinking step. Specifically, the apparatus used in the aqueous liquid adding step is preferably a high-speed stirring-type mixing apparatus, more preferably a high-speed stirring-type continuous mixing apparatus, and still more preferably a transverse or longitudinal-type and high-speed stirring-type continuous mixing apparatus. More specific examples of the apparatus used in the aqueous liquid adding step include a SHUGI mixer (manufactured by Powrex Corporation), a Turbulizer (manufactured by HOSOKAWA MICRON CORPORATION), a Loedige mixer (manufactured by Gebrüder Lödige Maschinenbau GmbH), and the like.

Of mixing conditions of the mixing apparatus used in the aqueous liquid adding step, (i) the number of revolutions is preferably in a range from 100 rpm to 10000 rpm, and more preferably in a range from 300 rpm to 2000 rpm, and (ii) a retention time is preferably within 180 seconds, more preferably in a range from 0.1 to 60 second(s), and still more preferably in a range from 1 to 30 second(s). Note that, since powder fluidity is attained by infiltrating moisture into water absorbent resin powder, a curing step may be further carried out after the aqueous liquid adding step depending on quantity of an aqueous liquid to be added.

What is meant by "(c) adding an aqueous liquid to the water absorbent resin powder during and/or after the step (b)" in the present invention is a step of adding the aqueous liquid during a surface crosslinking reaction and/or after the surface crosslinking reaction ends. The step (c) is preferably carried out in any of the following manners.

A method of the present invention for producing a polyacrylic acid (salt)-based water absorbent resin particle (method 1) is preferably configured so that the step (c) is carried out during the step (b). The method is further preferably configured so that the aqueous liquid is added to the water absorbent resin powder which exists in a heat reactor or in an active energy ray reactor. What is meant by "during the step (b)" is a period of time (i) from a reaction starting time which is an earlier-starting time of a start of heating and a start of irradiating with an active energy ray (ii) to a time immediately before the water absorbent resin powder is exhausted from the reactor. Note that, in a case where the reactor also carries out the cooling step, a time immediately before the cooling step starts corresponds to an end of the step (b). Generally, "during the step (b)" can be considered to be during retention in the reactor used in the step (b).

A method of the present invention for producing a polyacrylic acid (salt)-based water absorbent resin (method 2) is preferably configured so that the step (c) is carried out after the step (b). The method is more preferably configured so that the step (c) starts within 3 minutes after the step (b). The method is still more preferably configured so that the step (c) is carried out during a cooling step after the step (b).

(Aqueous Liquid)

In the present invention, "aqueous liquid" means water only, or an aqueous solution or dispersion liquid which contains water (liquid-water) as a main component and optionally contains an organic solvent and/or an additive. Water vapor can be supplied as the "aqueous liquid". In a case where water is added in the form of water vapor (see Patent Literature 20), a sufficient amount of water is not sometimes added. Therefore, the aqueous liquid is preferably supplied in the form of liquid.

In a case where the aqueous liquid is the aqueous solution or dispersion liquid, the organic solvent and the additive have respective concentrations determined as appropriate. Quantity of the water contained in the aqueous liquid is preferably in a range from 50 mass % to 100 mass %, more preferably in a range from 60 mass % to 100 mass %, still more preferably in a range from 70 mass % to 100 mass %, particularly preferably in a range from 80 mass % to 100 mass %, and most preferably in a range from 90 mass % to 100 mass %.

In the present invention, a temperature of the aqueous liquid is determined as appropriate according to solubility of the following additive and degree of mixing the water absorbent resin powder with the aqueous liquid. The temperature of the aqueous liquid is preferably in a range from 0° C. to 100° C., and more preferably in a range from 10° C. to 50° C.

In a case where a hydrophilic organic solvent is used, quantity of the hydrophilic organic solvent to be used relative to 100 parts by mass of the water absorbent resin powder is preferably more than 0 part by mass and not more than 10 parts by mass, and more preferably more than 0 part by mass and not more than 5 parts by mass. Examples of the hydrophilic organic solvent include (i) a primary alcohol, preferably a C1 to C4 primary alcohol, and more preferably a C2-C3 primary alcohol, (ii) a lower ketone whose carbon number is 4 or lower, e.g., acetone, and the like.

Specific examples of the hydrophilic organic solvent include (i) lower alcohols such as methyl alcohol, ethyl alcohol, n-propyl alcohol, isopropyl alcohol, n-butyl alcohol, isobutyl alcohol, and t-butyl alcohol, (ii) ketones such as acetone, (iii) ethers such as dioxane, tetrahydrofuran, and methoxy(poly)ethylene glycol, (iv) amides such as epsilon-caprolactam and N,N-dimethylformamide, (v) sulfoxides such as dimethyl sulfoxide, (vi) polyvalent alcohols such as polyoxypropylene and oxyethylene-oxypropylene block copolymers, and the like.

(Atmospheric Dew Point and Gas Phase Temperature in Aqueous Liquid Adding Step)

In the present invention, an atmospheric dew point is controlled to not lower than 20° C., preferably not lower than 30° C., more preferably not lower than 40° C., still more preferably not lower than 50° C., and particularly preferably not lower than 60° C., in the aqueous liquid adding step of adding the aqueous liquid to the water absorbent resin powder during and/or after the reaction step. An upper limit of the atmospheric dew point is not particularly limited, but generally needs only to be lower than 100° C., more preferably not higher than 90° C. It is not preferable that the atmospheric dew point be lower than 20° C. because (i) moisture contained in the water absorbent resin powder (mixture and/or reactant) is easily vaporized, (ii) a large amount of fine powder is generated during operation of an apparatus, and (iii) an anti-damage property is deteriorated.

The atmospheric dew point sometimes changes depending on a place in the apparatus or lapse of a treatment time. The atmospheric dew point is preferably controlled, in the apparatus, within a constant range (which falls within the above range). Change in temperature from the lower limit of the atmospheric dew point (difference between the upper limit and the lower limit of the atmospheric dew point) is preferably within 20° C., more preferably within 10° C., still more preferably within 5° C., and particularly preferably within 2° C. In a case where the atmospheric dew point changes depending on the place in the apparatus or the lapse of the treatment time, it is possible to simply and easily define the atmospheric dew point by measuring a dew point of a gas obtained at an air outlet of the apparatus. In a case where the apparatus has a plurality of air outlets, it is possible to find an average dew point from dew points of and volumes of gasses obtained from the respective plurality of air outlets. Alternatively, in a case where the apparatus has no air outlet of gas or in a case where an air outlet also serves as an outlet of a water absorbent resin, the atmospheric dew point may be defined (i) by measuring a dew point of a gas obtained at the outlet of the water absorbent resin, (ii) with a dew-point hydrometer put into the apparatus or (iii) by sucking (sampling) an inner gas and measuring the inner gas.

In a case where the aqueous liquid is added, a gas phase temperature (defined as a temperature of a gas in an upper space of the apparatus) is controlled to preferably a range from 50° C. to 150° C., and more preferably a range from 80° C. to 130° C. during the reaction step and/or in a step (particularly the cooling step) after the reaction step. It is not preferable that the gas phase temperature be higher than 150° C. because (i) moisture contained in the water absorbent resin powder (mixture and/or reactant) is easily vaporized, (ii) a large amount of fine powder is generated during operation of the apparatus, and (iii) the anti-damage property is deteriorated.

In a case where the gas phase temperature is lower than the atmospheric dew point, dew condensation is generated in the apparatus, and a problem such as adhesion of the water absorbent resin powder is caused. It is therefore preferable to determine the range of the gas phase temperature to be higher than the atmospheric dew point. Specifically, it is preferable to determine the gas phase temperature as appropriate so as to be preferably the atmospheric dew point plus 5° C., or higher, more preferably the atmospheric dew point plus 10° C., or higher, and still more preferably the atmospheric dew point plus 20° C., or higher.

The atmospheric dew point and the gas phase temperature are controlled depending on quantity of gas to be supplied, quantity of gas to be exhausted, humidity of supplied gas, etc. The atmospheric dew point and the gas phase temperature are measured vertically upward of the water absorbent resin powder. The atmospheric dew point and the gas phase temperature sometimes do not fall within the above respective ranges before or after a heat treatment starts (in a case of a continuous type, immediately after a mixture is put into a heat treatment apparatus and/or immediately before a reactant is exhausted from the heat treatment apparatus). In order to sufficiently bring about the effect of the present invention, the atmospheric dew point and the gas phase temperature need only to fall within the respective above ranges during preferably not less than 50%, more preferably not less than 70%, still more preferably not less than 80%, and particularly preferably not less than 100% of the whole reaction time.

In a case where a constant flow of gas is let through in the aqueous liquid adding step (during the reaction step and/or in the step after the reaction step), a dew point and a temperature which are measured at an appropriate place in an air exhausting mechanism of the apparatus may be employed as the atmospheric dew point and the gas phase temperature which are defined in the present invention. The apparatus can be specifically configured such that (i) no gas other than the constant flow of gas mixes, (ii) no treatment is carried out by a gas cleaning apparatus etc., (iii) the temperature is not forcibly changed with the heat treatment apparatus, a cooling apparatus, etc., and (iv) it takes preferably 5 seconds or shorter, and more preferably 1 second or shorter for the constant flow of gas to pass through the apparatus. That is, as has been described, preferably, it is possible to define the atmospheric dew point by measuring a dew point of a gas obtained at an air outlet.

In the present invention, no particular limitation is placed on a gas which fills an upper space of an apparatus (a reactor and/or a cooling apparatus) to which an aqueous liquid is added. In terms of physical properties of a polyacrylic acid (salt)-based water absorbent resin particle to be produced, examples of the gas include (i) air, (ii) inert gases such as water vapor, nitrogen and argon, (iii) a mixture of air and an inert gas, and the like. Note that it is possible to add water vapor as appropriate so as to adjust the atmospheric dew point.

(Temperature(s) of Mixture and/or Reactant (Water Absorbent Resin Powder) in Aqueous Liquid Adding Step)

The present invention is characterized in that, in addition to controlling the atmospheric dew point to the above range in the aqueous liquid adding step, a temperature(s) of a mixture and/or a reactant (water absorbent resin powder) are/is higher than the atmospheric dew point in the aqueous liquid adding step.

That is, during the reaction step and/or in the step after the reaction step, the temperature(s) of the mixture and/or the reactant (water absorbent resin powder) in the aqueous liquid adding step are/is preferably in a range from 50° C. to 150° C., and more preferably in a range from 70° C. to 120° C. In a case where the temperature(s) is/are lower than 50° C., the reactant (water absorbent resin powder) slowly absorbs the aqueous liquid, and lumps of the reactant are easily generated. This probably makes it difficult to operate the apparatus. Moreover, it is not preferable that the temperature(s) be higher than 150° C. because an effect brought about by adding the aqueous solution deteriorates.

(Moisture Content(s) of Mixture and/or Reactant (Water Absorbent Resin Powder) in Aqueous Liquid Adding Step)

During the reaction step and/or in the step after the reaction step, moisture content(s) of the mixture and/or the reactant (water absorbent resin powder) in the aqueous liquid adding step are/is controlled to preferably a range from 2 wt % to 15 wt %, more preferably a range from 3 wt % to 10 wt %, and still more preferably a range from 4 wt % to 8 wt %. In a case where the moisture content(s) is/are higher than 15 wt %, dew condensation is generated in the apparatus, and a problem such as adhesion of the water absorbent resin powder is caused. This probably makes it difficult to operate the apparatus.

(Quantity of Aqueous Liquid to be Added)

Quantity of the aqueous liquid to be added to the water absorbent resin powder during the reaction step and/or in the step after the reaction step is preferably in a range from 1 wt % to 14 wt %, and more preferably in a range from 3 wt % to 12 wt %. In a case where the quantity is less than 1 wt %, it is not possible to produce a polyacrylic acid (salt)-based water absorbent resin which less generates fine powder and has an excellent anti-damage property. In a case where the quantity is more than 14 wt %, lumps of water absorbent resin are easily generated. This probably makes it difficult to operate the apparatus.

(Method of Adding Aqueous Liquid)

In the present invention, the aqueous liquid needs only to be added to the water absorbent resin powder in a state where the atmospheric dew point and the temperature of the water absorbent resin powder (mixture and/or reactant) in the aqueous liquid adding step fall within the above respective ranges during the reaction step and/or in the step after the reaction step. This method of adding the aqueous liquid is applicable to any of a continuous apparatus and a batch apparatus.

In a case where the continuous apparatus is used during the reaction step and/or in the step after the reaction step, the aqueous liquid needs only to be added to the water absorbent resin powder at a place in the continuous apparatus which place is preferably forward 1/10 to 9/10, and more preferably forward 1/5 to 4/5 of the whole length of the continuous apparatus. In a case where the batch apparatus is used, timing when the aqueous liquid is added to the water absorbent resin powder needs only to be determined as appropriate depending on a ratio to a retention time (e.g., a reaction time or a cooling time). Specifically, the timing is 1/10 to 9/10, and more preferably 1/5 to 4/5 of the whole reaction time or the whole mixing time (particularly the whole cooling time). Note that the "forward" means a place of the continuous apparatus to which place the water absorbent resin powder is supplied, regardless of whether the continuous apparatus is of a longitudinal-type or a traverse-type.

In a case where the place where the aqueous liquid is added is less than 1/10, the addition of the aqueous liquid does not bring about any sufficient effect. In a case where the place where the aqueous liquid is added is more than 9/10, curing of the water absorbent resin powder (mixture and/or reactant) does not complete, and another curing step is required. It is not preferable to omit the another curing step because a problem such as clogging is caused in a subsequent step. This probably fails to produce a polyacrylic acid (salt)-based water absorbent resin particle having target physical properties. Note that the "curing" means dispersion of the aqueous liquid, and absorption of the aqueous liquid into the water absorbent resin powder.

In the present invention, the aqueous liquid may be added at one place which falls within the above range, or may be added at a plurality of places in a longitudinal or traverse direction of the apparatus. Moreover, the aqueous solution can be added in both the reaction step and the cooling step.

In the present invention, no particular limitation is placed on an adding apparatus to be used to add the aqueous liquid to the water absorbent resin powder in the mixing apparatus. As the adding apparatus preferably used is an apparatus which can uniformly drop or spray the aqueous liquid over a narrow range (surface area), and more preferably used is an apparatus which can uniformly spray the aqueous liquid over the narrow range. Specific examples of the adding apparatus include a flat spray, and a one-fluid type or two-fluid type spray having a spray pattern of hollow cone or full cone. A further preferable example of the adding apparatus is a narrow-angle spray which can spray the aqueous liquid over a narrow region.

The dropping or the spraying may be carried out at one place or at a plurality of places simultaneously or individually. The dropping and the spraying may be used in combination. The dropping or the spraying may be carried out from above or below the water absorbent resin powder. Note here that (i) "simultaneously" in a case of continuous mixing means spraying or dropping the aqueous liquid from a plurality of places at the same time in parallel from the side along a movement direction, and (ii) "individually" in the case of the continuous mixing means spraying or dropping the aqueous liquid from the plurality of places in series at different time axes along the movement direction.

No particular limitation is placed on the size of a droplet of the aqueous liquid to be sprayed. It is, however, preferable that the size be a volume average particle diameter falling within a range from 10 μm to 1000 μm. It is not preferable that the size of the droplet be larger than 1000 μm because (i) an obtained water absorbent resin has a non-uniform moisture content, (ii) water absorbent resin powder absorbs a large amount of water to form lumps, (iii) and such lumps sometimes clog the apparatus. It is neither preferable that the size of the droplet be smaller than 10 μm because a sprayed aqueous liquid does not effectively adhere to the water absorbent resin but is exhausted as splash outside of the apparatus or becomes dew condensation water.

On this account, the size of the droplet is more preferably in a range from 50 μm to 500 μm. Note that there is a general tendency that, in a case where air current is slow in the apparatus, the size of the droplet is allowed to be small, whereas in a case where the air current is fast in the apparatus, the size of the droplet should be large so as to prevent the droplet from being exhausted as splash outside of a system.

(Adhesion Preventing Agent)

In the present invention, it is preferable to add the aqueous liquid so as to come into contact with only the water absorbent resin powder. In a case where the aqueous liquid possibly comes into contact with something other than the water absorbent resin powder, e.g., an inner wall surface of a reactor, it is preferable that the aqueous liquid contain an adhesion preventing agent such as polyethylene glycol (PEG) or polypropylene glycol (PPG).

(Additive)

In order that the polyacrylic acid (salt)-based water absorbent resin particle to be produced in the present invention has an additional function, the following various additives can be dissolved or dispersed in the above aqueous liquid. These additives are not particularly limited. As the additives used is, for example, at least one kind selected from the group consisting of a deodorant, an antimicrobial agent, an anti-coloring agent, a chelating agent, an inorganic monovalent or polyvalent salt, an acidic compound, a reducing agent, an alkaline compound, a surfactant, and a water-insoluble inorganic fine particle. Among these additives, preferably used is a water-soluble additive, and more preferably used is a water-soluble additive selected from the group consisting of the chelating agent, the deodorant, a polyvalent metal salt, and an inorganic reducing agent.

More specifically, it is preferable to add the chelating agent in terms of preventing the polyacrylic acid (salt)-based water absorbent resin particle to be produced from coloring and deteriorating. An example of the chelating agent is a chelating agent disclosed in "[2] Chelating Agent" of International Publication No. WO2011/040530. The chelating agent and quantity of the chelating agent to be used, disclosed in the International Publication, are applied to the present invention. A preferable chelating agent is selected from (i) a water-soluble non-polymer of amino polyvalent carboxylic acid or amino polyvalent phosphoric acid and (ii) a salt thereof (particularly a monovalent salt thereof).

It is preferable to add the inorganic reducing agent in terms of (i) preventing the polyacrylic acid (salt)-based water absorbent resin particle to be produced from coloring and deteriorating and (ii) reducing a residual monomer of the polyacrylic acid (salt)-based water absorbent resin particle to be produced. An example of the inorganic reducing agent is an inorganic reducing agent disclosed in "[3] Inorganic Reducing Agent" of International Publication No. WO2011/040530. The inorganic reducing agent and quantity of the inorganic reducing agent to be used, disclosed in the International Publication, are applied to the present invention. A preferable inorganic reducing agent is selected from a water-soluble phosphoric reducing agent and a sulfuric reducing agent.

Moreover, it is preferable to add an inorganic salt, particularly the polyvalent metal salt and/or a cationic polymer in terms of (i) improving water absorbing speed (Vortex) of and liquid permeability (SFC) of the polyacrylic acid (salt)-based water absorbent resin particle to be produced and (ii) fluidity of the polyacrylic acid (salt)-based water absorbent resin particle during moisture absorption. An example(s) of the polyvalent metal salt and/or the cationic polymer are/is a polyvalent metal salt and/or a cationic polymer disclosed in "[7] Polyvalent Metal Salt and/or Cationic Polymer" of International Publication No. WO2011/040530. The polyvalent metal salt and/or the cationic polymer, and quantities (quantity) of the polyvalent metal salt and/or the cationic polymer to be used, which are disclosed in the International Publication, are applied to the present invention. A preferable polyvalent metal salt is selected from an organic acid of aluminum and an inorganic acid of aluminum.

An example of the water-insoluble inorganic fine particle is a water-insoluble inorganic fine particle disclosed in "[5] Water-Insoluble Inorganic Fine Particle" of International Publication No. WO2011/040530. An example of the surfactant is a surfactant disclosed in International Publication No. WO2005/075070. These disclosed water-insoluble inorganic fine particle and surfactant are suitably applied to the present invention.

As the deodorant used is a synthetic or natural deodorant. Preferably used is a vegetable component disclosed in International Publication No. WO2003/104349. Specifically used is polyphenols such as tannin.

In terms of reducing the residual monomer of the polyacrylic acid (salt)-based water absorbent resin particle to be produced, the aqueous liquid can contain sulfite such as sodium bisulfite (SBS). In order to adjust the water absorbing speed, the aqueous liquid can contain an organic or inorganic base, an organic or inorganic acid, or a monovalent or polyvalent metal salt (e.g., aluminum sulfate). In order to add a deodorant function, the aqueous liquid can contain a deodorant. In order to add a visual value, the aqueous liquid can contain a coloring agent. In order to improve an anti-urine property, the aqueous liquid can contain various chelating agents, etc.

The total concentration of all of the additives to be added to the aqueous liquid is preferably in a range from 0.01 wt % to 50 wt %, more preferably in a range from 0.1 wt % to 40 wt %, and still more preferably in a range from 1 wt % to 30 wt %. Quantity of an additive to be added to water absorbent resin powder can also be determined as appropriate according to an object to be attained and/or the additive. The quantity is preferably in a range from 1 ppm to 10 wt %, more preferably in a range from 10 ppm to 1 wt %, and still more preferably in a range from 20 ppm to 0.5 wt %.

(2-8) Step after Addition (Sizing Step, Etc.)

After the aqueous liquid is added to the water absorbent resin powder, part of the water absorbent resin powder can be additionally heated or thermally dried so as to adjust moisture content and improve powder fluidity. A curing step or the heating or thermal drying makes it possible to infiltrate mixed moisture into a water absorbent resin and to improve the powder fluidity. Therefore, the water absorbent resin having been heated or thermally dried is suitable for a subsequent production step, being stored, or product filling.

In the present invention, the aqueous liquid is added during the reaction step and/or in the step after the reaction step. This makes it possible to infiltrate moisture into the water absorbent resin and to attain the powder fluidity. Therefore, no separate curing step is required. It is consequently possible to simplify a process and to prevent physical properties from being deteriorated due to process damage. Note that "Flow Rate" defined as the powder fluidity by ERT450.2-02 is preferably not less than 3 (g/s), more preferably not less than 5 (g/s), and still more preferably not less than 7 (g/s).

After surface crosslinking or after addition of the aqueous liquid, generation of aggregates and/or change in particle size are/is sometimes found. Therefore, a classification step and an optional pulverization step of pulverizing the aggregates (these steps are generically called a sizing step) may be carried out. Aggregates (coarse particles), aggregates from which fine powder has been removed, or fine powder (particularly, particles of smaller than 150 μm), obtained in the classification step, can be discarded. Alternatively, the coarse particles and the fine powder which has been removed can be used in the pulverization step and in a fine powder recycling step, respectively.

(2-9) Other Step

In addition to the above-described steps, steps such as a recycling step of recycling an evaporated monomer, a granulation step, and a fine powder recycling step can be carried out, if necessary.

The additives described in (Additive) of (2-7) above can be added in a step other than (2-7) Aqueous Liquid Adding Step. A step of adding pulp, a thermoplastic fiber, etc. can be further carried out. Quantity of the pulp, the thermoplastic fiber, etc. to be added relative to 100 parts by weight of the water absorbent resin is preferably in a range from 0 to 3 part(s) by weight, and more preferably in a range from 0 to 1 part by weight.

[3] Physical Properties of Polyacrylic Acid (Salt)-Based Water Absorbent Resin Particle For the purpose of applying, to sanitary products, particularly disposable diapers, the polyacrylic acid (salt)-based water absorbent resin particle produced by the method of the present invention, it is desirable that at least one, more preferably two or more (including AAP), and still more preferably three or more of the following physical properties (a) through (e) be controlled within a desired range(s).

Note that physical properties, other than the physical properties (a) through (e), to be controlled are FSC (Free Swelling Capacity), PSD (Particle Size Distribution), pH, Flow Rate (flow speed), Density (bulk specific gravity), and the like.

The present invention is suitably applied to a production method which highly controls these physical properties. In a case where these physical properties do not meet the following ranges, the present invention sometimes does not bring about a sufficient effect, or a high concentration disposable diaper which contains a large number of water absorbent resin particles per disposable diaper sometimes does not exert a sufficient performance.

Physical properties to be controlled and a method for measuring the physical properties are determined as appropriate. The measurement method disclosed in EDANA can be applied to the polyacrylic acid (salt)-based water absorbent resin particle of the present invention to be produced.

(a) Moisture Content (and Additive)

Moisture content of the polyacrylic acid (salt)-based water absorbent resin particle produced by the method of the present invention is preferably in a range from 5 wt % to 20 wt %, more preferably in a range from 5 wt % to 18 wt %, and still more preferably in a range from 5 wt % to 15 wt % (the lower limit of the range is further preferably 6 wt %, and particularly preferably approximately 7 wt %). The polyacrylic acid (salt)-based water absorbent resin particle whose moisture content falls within the range less generates fine powder and has a high impact resistance. It is preferable that the moisture content fall within the range because it is further possible to improve productivity.

The polyacrylic acid (salt)-based water absorbent resin particle of the present invention preferably contains the additive described in (2-7) above in addition to water. Kinds and quantity of the additive are determined as appropriate, but typically within the respective ranges described in (2-7).

(b) Water Absorption Capacity without Load (CRC) ERT 441.2-02

The polyacrylic acid (salt)-based water absorbent resin particle produced by the method of the present invention absorbs a 0.9 wt % saline at a water absorption capacity without load (CRC) of preferably not less than 10 (g/g), more preferably not less than 20 (g/g), still more preferably not less than 25 (g/g), particularly preferably not less than 27 (g/g), not less than 30 (g/g), and not less than 35 (g/g), in this order. The higher the water absorption capacity without load (CRC) is, the more preferable it is. Not particular limitation is placed on an upper limit of the water absorption capacity without load (CRC). In terms of balance with other physical properties, however, the upper limit is preferably not more than 50 (g/g), more preferably not more than 45 (g/g), and still more preferably not more than 40 (g/g). The upper and lower limits of the CRC can be selected as appropriate within the respective ranges. The CRC is, for example, in a range from 30 (g/g) to 45 (g/g), and further preferably in a range from 35 (g/g) to 40 (g/g).

(c) Water Absorption Capacity Under Load (AAP) ERT 442.2-02

In terms of preventing leakage from disposable diapers, the polyacrylic acid (salt)-based water absorbent resin particle produced by the method of the present invention absorbs a 0.9 wt % saline at a water absorption capacity under load (AAP) (under load of 2.06 kPa) of preferably not less than 20 (g/g), more preferably not less than 22 (g/g), still more preferably not less than 23 (g/g), not less than 25 (g/g), not less than 28 (g/g), not less than 30 (g/g), and not less than 31 (g/g), in this order. The higher the water absorption capacity under load (AAP) is, the more preferable it is. Not particular limitation is placed on an upper limit of the water absorption capacity under load (AAP). In terms of balance with other physical properties, however, the upper limit is preferably not more than 40 (g/g), and more preferably not more than 35 (g/g). The upper and lower limits of the AAP can be selected as appropriate within the respective ranges. The AAP is, for example, in a range from 30 (g/g) to 40 (g/g), and further preferably in a range from 31 (g/g) to 35 (g/g).

(d) Water Soluble Component (Ext) ERT470.2-02

Water soluble component (Ext) of the polyacrylic acid (salt)-based water absorbent resin particle produced by the method of the present invention is preferably not more than 35 wt %, more preferably not more than 25 wt %, still more preferably not more than 15 wt %, and particularly preferably not more than 10 wt %. The Ext can be controlled by controlling the above-described polymerization condition (e.g., quantity of a crosslinking agent) and drying condition (temperature), etc.

(e) Residual Monomer ERT410.2-02

A residual monomer of the polyacrylic acid (salt)-based water absorbent resin particle produced by the method of the present invention is preferably in a range from 0 ppm to 700 ppm, more preferably in a range from 0 ppm to 600 ppm, and still more preferably in a range from 0 ppm to 500 ppm.

(f) Balance Between CRC and AAP

The higher the total of the CRC and the AAP is, the more preferable it is. The total of the CRC and the AAP is not less than 65 (g/g), further preferably not less than 68 (g/g), and not less than 70 (g/g), in this order. The higher an upper limit of the total of the CRC and the AAP is, the more preferable it is. In terms of balance with other physical properties, however, the upper limit is not more than 90 (g/g), and further preferably not more than 85 (g/g).

The higher a ratio of the AAP to the CRC is, the more preferable it is. The ratio is not less than 0.7 or not less than 0.8 (an upper limit of the ratio is approximately 1.1).

The smaller a difference between the CRC and the AAP is, the more preferable it is. The difference is preferably not more than 10 (g/g), not more than 8 (g/g), not more than 5 (g/g), and not more than 3 (g/g), in this order (a lower limit of the difference is typically minus 2 (g/g), and further preferably approximately 0 (g/g)).

(g) Particle Size and Shape

A preferable particle size falls within the range described in (2-5) Classification Step. The water absorbent resin may be in the form of a spherical particle or in the form of a granulated spherical particle. The water absorbent resin preferably has a large specific surface area, a high water absorbing speed, and a non-uniformly pulverized shape. What is meant by "non-uniformly pulverized shape" is an irregular shape of a pulverized gel or dried water absorbent resin, particularly a pulverized dried water absorbent resin.

(h) Mass Average Particle Diameter Decrease Ratio (%) at which Impact Decreases Mass Average Particle Diameter, and Mass Average Particle Diameter Increase Ratio (%) at which Granulation Increases Mass Average Particle Diameter The water absorbent resin of the present invention may be granulated or may contain a granulated material. The fact that the water absorbent resin is granulated can be found by finding with an electronic microscope etc. (i) that a plurality of particles come into contact with each other via interfaces thereof or (ii) change in particle size (increase in D50, reduction in quantity of fine powder, etc. after an aqueous liquid is added).

Degree of granulation can be determined as appropriate depending on quantity of an aqueous liquid or a subsequent sizing step. A mass average particle diameter (D50) decrease ratio at which impact decreases a mass average particle diameter (D50) is defined in conformity to Patent Literature 17 and will be described in Examples. The mass average particle diameter (D50) decrease ratio is in a range from 0% to 30%, preferably in a range from 5% to 25%, more preferably in a range from 5% to 20%, and still more preferably in a range from 5% to 15%. For example, in a case where a water absorbent resin whose mass average particle diameter (D50) decrease ratio at which impact decreases a mass average particle diameter (D50) is more than 30% is used to produce disposable diapers etc., (i) granulated particles are broken, quantity of fine powder of the water absorbent resin increases, so that an adverse effect is brought about on the production of disposable diapers, (ii) an absorbent body to be produced cannot be uniformly dispersed in hydrophilic fiber, and (iii) a particulate water absorbent agent comes off from an absorbent body, so that it is not possible to retain a desired amount of the particulate water absorbent agent.

A mass average particle diameter (D50) increase ratio at which granulation increases the mass average particle diameter (D50) (later described in Examples) is in a range from 5% to 50%, preferably in a range from 5% to 40%, more preferably in a range from 5% to 30%, and still more preferably in a range from 10% to 25%. In a case where the mass average particle diameter (D50) increase ratio at which granulation increases the mass average particle diameter (D50) is more than 50%, a problem with continuous operation is probably caused. In a case where the mass average particle diameter (D50) increase ratio at which granulation increases the mass average particle diameter (D50) is less than 5%, a large amount of fine powder is probably generated in a subsequent step.

(i) Preferable Additive

Preferably contained is at least one kind selected from the group consisting of a deodorant, an antimicrobial agent, an anti-coloring agent, a chelating agent, an inorganic salt, an acidic compound, a reducing agent, an alkaline compound, and a surfactant. Further preferably, the chelating agent is further contained.

(j) Preferable Water Absorbent Resin Produced in the Present Invention

The present invention provides a novel water absorbent resin having a high moisture content, a high CRC and a high AAP. That is, the present invention provides a polyacrylic acid (salt)-based water absorbent resin having excellent physical properties, i.e., a moisture content in a range from 5 wt % to 20 wt % (further, in a range from 6 wt % to 15 wt %), a CRC in a range from 30 (g/g) to 45 (g/g) (further, in a range from 35 (g/g) to 40 (g/g)), an AAP in a range from 30 (g/g) to 40 (g/g) (further, in a range from 31 (g/g) to 35 (g/g)), and the total of the CRC and the AAP of not less than 65 (g/g).

[4] Reactor

The present invention is characterized in controlling an atmospheric dew point and a temperature of a water absorbent resin particle. The present invention enables industrial-scale production of a polyacrylic acid (salt)-based water absorbent resin particle having excellent physical properties. The present invention further provides a reactor.

A reactor for the water absorbent resin powder of the present invention is a water absorbent resin powder stirring type reactor which has (i) a stirring function of stirring the water absorbent resin powder (preferably, a stirring blade), (ii) a heating or cooling function of heating or cooling the water absorbent resin powder from a surface (preferably, a jacket), and (iii) an adjusting function of adjusting a temperature of and a dew point of an upper space. The reactor further preferably has an adding function of adding an aqueous liquid (preferably, a spray function). A batch-type reactor has an inner volume of 1 L to 1 $m^3$ (still more preferably, 2 L to 100 L). From the result of a batch, it is possible to predict (i) industrial-scale continuous production (preferably, not less than 100 (kg/hr)) and (ii) scale-up of industrial-scale operation condition in a small-scale experiment.

[5] Use of Polyacrylic Acid (Salt)-Based Water Absorbent Resin Particle

Use of the polyacrylic acid (salt)-based water absorbent resin particle of the present invention is not particularly limited. However, the polyacrylic acid (salt)-based water absorbent resin particle is preferably applied to absorbent articles such as disposable diapers, sanitary napkins or incontinence pads. The polyacrylic acid (salt)-based water absorbent resin particle exerts a particularly excellent performance, particularly, in a case where (i) the polyacrylic acid (salt)-based water absorbent resin particle is contained in high concentration disposable diapers (each of which contains a large amount of a water absorbent resin) which conventionally have a problem such as odor, coloring, etc. derived from a raw material for a water absorbent resin particle and (ii) the polyacrylic acid (salt)-based water absorbent resin particle is contained, particularly, in an upper part of an absorbent body of the absorbent articles.

Quantity of the water absorbent resin particle to be contained in the absorbent body of the absorbent articles which absorbent body optionally contains another absorbent material such as pulp fiber (core concentration) is preferably in a range from 30 wt % to 100 wt %, more preferably in a range from 40 wt % to 100 wt %, still more preferably in a range from 50 wt % to 100 wt %, further still more preferably in a range from 60 wt % to 100 wt %, particularly preferably in a range from 70 wt % to 100 wt %, and most preferably in a range from 75 wt % to 95 wt %.

[6] Distinction from Conventional Techniques

As has been described in Background Art (Patent Literatures 1 through 25), Patent Literatures 1 through 5, 19, 21 and 22, etc. disclose surface crosslinking methods. Among these Patent Literatures, Patent Literature 4 discloses, as a technique for adding water during surface crosslinking, a method for further adding (5 wt % to 20 wt % of) an aqueous liquid in a heat treatment at a moisture content of 10 wt % to 30 wt % so as to reduce a residual crosslinking agent. Further, as the technique proposed are Patent Literatures 2 and 19 which pay attention to a dew point during surface crosslinking, and Patent Literatures 21 and 22 that were filed by the applicant of the present application and have not been published. Moreover, Patent Literatures 6 through 13, 17, 18 and 20 disclose, as a modification method for modifying a surface-crosslinked water absorbent resin, a technique for adding, to a surface-crosslinked water absorbent resin, an aqueous solution that contains water and an additive. Particularly, (i) Patent Literature 6 discloses, as the modification method, a technique for adding water to the surface-crosslinked water absorbent resin in a cooling step, and (ii) Patent Literature 20 discloses, as the modification method, a technique for granulating a water absorbent resin with water vapor. Patent Literatures 14 through 16 disclose, as a technique for preventing dust of a water absorbent resin, a technique for adding a dust inhibiting agent. Patent Literature 23 discloses, as a method for transporting a water absorbent resin with air so as not to damage the water absorbent resin, a method for transporting the water absorbent resin with a gas having a low dew point in a range from minus 5° C. to minus 100° C. Patent Literature 24 discloses a technique for heating in the presence of water vapor so as to reduce a residual monomer. Patent Literature 25 discloses a technique for thermally drying a hydrogel at 80° C. to 250° C. with a gas whose dew point is in a range from 50° C. to 100° C. so as to reduce a residual monomer.

On the other hand, these Patent Literatures 1 through 25 and other prior art documents neither disclose at all a dew point when an aqueous liquid is added to a water absorbent resin nor suggest at all (i) the method of the present invention, which controls a dew point in an aqueous liquid adding step and (ii) an effect brought about by the method of the present invention. Though Patent Literatures 2, 19, 21 through 23, and 25 disclose a technique for defining a dew point in a drying step of drying a water absorbent resin, in a surface crosslinking step of surface-crosslinking the water absorbent resin, and in a transporting step of transporting the water absorbent resin, these Patent Literatures have not conventionally suggested at all (i) importance of a dew point when an aqueous liquid is added and (ii) an effect brought about by controlling the dew point.

Since these Patent Literatures 1 through 25 and the other prior art documents do not define at all a dew point when an aqueous liquid is added, a conventional water absorbent resin produced by means of these techniques does not attain all of (i) a high water absorption capacity (CRC), (ii) a high water absorption capacity under load (AAP), (iii) reducing quantity of fine powder (which passes through a sieve having a mesh size of 150 μm or 106 μm), and (iv) suppressing quantity of fine powder to be generated due to damage of the water absorbent resin. The conventional water absorbent resin neither suggests at all the novel water absorbent resin of the present invention. The conventional technique for granulating with water vapor (Patent Literature 20) does not disclose a dew point undoubtedly.

Surface crosslinking at a high moisture content (Patent Literature 4) makes it difficult to produce a water absorbent resin having high CRC and AAP (particularly, a CRC in a range from 30 (g/g) to 45 (g/g) (further, in a range from 35 (g/g) to 40 (g/g)), an AAP in a range from 30 (g/g) to 40 (g/g) (further, in a range from 31 (g/g) to 35 (g/g)), and the total of the CRC and the AAP of not less than 65 (g/g)). In a case where (i) surface crosslinking is carried out at a low moisture content to obtain a water absorbent resin having a high CRC and (particularly) a high AAP, and then (ii) water is added so that the water absorbent resin has a high moisture content (particularly a moisture content in a range from 5 wt % to 20 wt % (further, in a range from 6 wt % to 15 wt %)), it is difficult to add a large amount of water, and physical properties such as the AAP are deteriorated due to aggregation during addition of water. It is therefore not possible to attain both a balance between the CRC and the AAP and the moisture content. It is difficult to attain both the balance and the moisture content in a case where a dew point is not controlled like in the conventional techniques, i.e., Patent Literatures 8 and 17.

EXAMPLES

The following Examples will more specifically describe the present invention. The present invention should not be narrowly interpreted within the limits of Examples. A proper combination of technical means disclosed in Examples is encompassed in the scope of the present invention.

Unless otherwise specified, an electrical apparatus (including an apparatus used to measure physical properties) used in Production Examples, Examples, and Comparative Examples (i) uses a 200-volt or 100-volt power supply, and (ii) measures the physical properties at room temperature (in a range from 20° C. to 25° C.) and at a relative humidity of 50% RH.

For convenience, "liter" and "% by weight" are sometimes abbreviated as "l" or "L", and "wt %", respectively.

[Method for Measuring Physical Properties]

(a) Water Absorption Capacity without Load (CRC)

A water absorption capacity without load (CRC) of the water absorbent resin particle produced by the method of the present invention was measured according to ERT441.2-02.

(b) Water Absorption Capacity Under Load (AAP)

A water absorption capacity under load (AAP) of the water absorbent resin particle produced by the method of the present invention was measured according to ERT442.2-02.

(c) Moisture Content

A moisture content of the water absorbent resin particle (including water absorbent resin powder, a mixture and like intermediates) produced by the method of the present invention was measured according to ERT430.2-02 except that quantity of the water absorbent resin particle was changed to 1.0 g and a drying temperature was changed to 180° C.

(d) Particle Size Distribution and Weight Average Particle Diameter (D50)

A particle size distribution of and a weight average particle diameter (D50) of the water absorbent resin particle and the water absorbent resin powder produced by the method of the present invention were measured in conformity to the measurement method disclosed in United States Patent Application Publication No. 2006/204755.

(e) Degradable Soluble Component

A degradable soluble component of the water absorbent resin particle produced by the method of the present invention was evaluated as below.

That is, L-ascorbic acid was added to a 0.9 wt % sodium chloride aqueous solution prepared in advance, so that a degradation test liquid containing 0.05 wt % of L-ascorbic acid was created. Specifically, 0.5 g of L-ascorbic acid was dissolved in 999.5 g of the 0.9 wt % sodium chloride aqueous solution.

Then, 200 ml of the degradation test liquid was put into a polypropylene vessel having a volume of 250 ml and provided with a lid (commodity name: Pack Ace, size: 65 mm in bore×60 mm in lower diameter×90 mm in height, manufacture by TERAOKA Co., Ltd.) To the vessel added was 1.0 g of a water absorbent resin particle. The water absorbent resin particle was allowed to uniformly swell. Subsequently, the whole vessel sealed with the lid was put into a thermostatic oven kept to 60° C., and was statically left for two hours. Thereafter, stirring was carried out with a cylindrical stirrer (length: 30 mm, external diameter: 8 mm) at approximately 500 rpm for 1 hour, and a soluble component was extracted from a swollen gel.

The extracted soluble component was filtrated with one sheet of filter paper (commodity name: JIS P 3801, No. 2, thickness: 0.26 mm, retained particle diameter: 5 μm, manufactured by Advantec Toyo Kaisha, Ltd.), and 50 g of the filtrate was employed as a liquid to be measured. The liquid to be measured was titrated with a 0.1N—NaOH aqueous solution to reach pH10, and further titrated with a 0.1N—HCl aqueous solution to reach pH2.7. Titres ([NaOH] mL, [HCl] ml) were found.

The same operations were carried out with respect to only a 0.9 wt % sodium chloride aqueous solution, and control titers ([bNaOH] mL, [bHCl] mL) were found.

The degradable soluble component of the water absorbent resin particle of the present invention was found by solving the following expression with (i) an average molecular weight of a monomer to be used and (ii) the titers found through the operations.

Ext[wt %]=0.1×(average molecular weight of monomer)× 200.0×100×{[HCl]−[$b$HCl]}/1000/1.0/50.0  [Expression 1]

Note that, in a case where the average molecular weight of the monomer is not found, the average molecular weight of the monomer is calculated with a neutralization ratio found through the titration operation. The neutralization ratio was found by solving the following expression.

Neutralization ratio[mol %]={1−([NaOH]−[$b$NaOH])/([HCl]−[$b$HCl])}×100  [Expression 2]

(f) Deodorization Performance

Deodorization performance of the water absorbent resin particle produced by the method of the present invention was evaluated as below.

That is, 50 g of adult urine and 2 g of a water absorbent resin were put into a polypropylene vessel having a volume of 120 ml and provided with a lid (commodity name: Pack Ace, size: 50 mm in bore×54 mm in lower diameter×74 mm in height, manufacture by TERAOKA Co., Ltd.). The water absorbent resin was allowed to uniformly swell with the adult urine. Then, the whole vessel sealed with the lid was put into a thermostatic oven kept to 40° C., and was statically left for 8 hours.

Thereafter, the vessel was uncovered, and then the contents of the vessel were smelled from a location approximately 3 cm above an opening of the vessel. The deodorization performance was evaluated according to the following criterion.

Under the assumption that an odor level of only human urine smelled in the same manner is "5", the deodorization performance was determined in six levels of "0: odorless", "1: manage to find odor", "2: possible to find odor but endurable", "3: possible to easily find odor", "4: strong odor", and "5: very strong odor". The evaluation was carried out with respect to urine of each of randomly chosen 20 adults, and an average of the evaluations was adopted.

(g) Mass Average Particle Diameter Decrease Ratio at which Impact Decreases Mass Average Particle Diameter, and Mass Average Particle Diameter Increase Ratio at which Granulation Increases Mass Average Particle Diameter A mass average particle diameter decrease ratio at which impact decreases a mass average particle diameter was found from a decrease ratio (%) of a mass average particle diameter (D50) before an impact test to a mass average particle diameter (D50) after the impact test according to the method described in (f) "Mass average particle diameter decrease ratio at which impact decreases mass average particle diameter, and mass average particle diameter increase ratio at which granulation increases mass average particle diameter" of column 27 of Patent Literature 17 (specification of U.S. Pat. No. 7,473,470). The mass average particle diameter decrease ratio at which impact decreases mass average particle diameter and a mass average particle diameter increase ratio at which granulation increases the mass average particle diameter were found according to the following expressions.

Mass average particle diameter decrease ratio (%) at which impact decreases mass average particle diameter=100×(($D50$ before impact)−($D50$ after impact))/($D50$ before impact)

Mass average particle diameter increase ratio (%) at which granulation increases mass average particle diameter=100×(($D50$ after granulation)−($D50$ before granulation))/($D50$ after granulation)

Production Example 1

To a 2-liter polypropylene vessel added were (i) 351 g of acrylic acid containing 70 ppm of p-methoxyphenol as a polymerization inhibitor, (ii) 0.76 g of polyethylene glycol diacrylate (molecular weight: 523) as an internal crosslinking agent, (iii) 296 g of a 48.5 wt % sodium hydroxide aqueous solution, and (iv) 337 g of deionized water (ion exchange water), so that a mixture was obtained. The mixture was mixed (stirred), so that a monomer aqueous solution (1) was prepared. A temperature of the monomer aqueous solution (1) thus prepared increased to 84° C. due to neutralization heat.

Then, 15.4 g of a 3.8 wt % sodium persulfate aqueous solution was added as a polymerization initiator to the monomer aqueous solution (1) which was being stirred and whose temperature was decreased to 83° C. Immediately after the addition, the mixture solution was poured in an atmospheric air open system into a stainless steel vat-type reactor (bottom surface: 340 mm×340 mm, height: 25 mm, internal surface: coated with Teflon (Registered Trademark)). In approximately 15 seconds after the pouring, a polymerization reaction started. A surface temperature of the stainless steel vat-type reactor was set in advance to 40° C. with a hot plate (NEO HOTPLACE HI-1000, manufactured by Iuchi Seieido Co., Ltd.)

The polymerization reaction progressed while (i) generating water vapor and (ii) causing expansion and foaming in all directions upward of the stainless steel vat-type reactor. Then, the reactant was shrunk to a size slightly larger than the bottom surface of the stainless steel vat-type reactor. This polymerization reaction (expansion and shrinkage) ended within approximately 1 minute. After the polymerization reaction ended, the reactant was retained in the stainless steel vat-type reactor for 4 minutes, and then taken out of the stainless steel vat-type reactor as a water-containing gel-like crosslinked polymer (1).

The water-containing gel-like crosslinked polymer (1) (hereinafter referred to as "hydrogel") obtained through the polymerization reaction was gel-crushed with a meat chopper (manufactured by Iizuka Kogyo Co., Ltd., MEAT-CHOPPER TYPE: 12VR-400KSOX, die pore diameter: 6.4 mm, the number of pores: 38, die thickness: 8 mm) to obtain a particulate hydrogel (1). Specifically, 250 g of the hydrogel was put into the meat chopper per minute while 50 g of deionized water adjusted to 90° C. was being added per minute.

Thereafter, the particulate hydrogel (1) was spread on a woven stainless-steel wire net having a mesh size of 850 μm, and dried at 180° C. for 30 minutes with a hot-air dryer to obtain a dried polymer (1). The dried polymer (1) was pulverized with a roll mill (manufactured by Inoguchi Giken Ltd., WML-type roll crusher), and then classified with a JIS standard sieve having a mesh size of 850 μm and a JIS standard sieve having a mesh size of 150 μm.

Through the above operations obtained was non-uniformly pulverized water absorbent resin powder (1) which had a weight average particle diameter (D50) of 350 μm and contained (i) 95 wt % of a particle whose diameter was not less than 150 μm and less than 850 μm and (ii) 5 wt % of a particle which passes through a sieve having a mesh size of 150 μm (including 1 wt % of a particle which passes through a sieve having a mesh size of 106 μm). The obtained water absorbent resin powder (1) had a water absorption capacity without load (CRC) of 51 (g/g) and a moisture content of 4.0 wt %.

[Example 1] Addition of Aqueous Liquid in Reaction Step (Atmospheric Dew Point: 75° C., Gas Phase Temperature: 100° C.)

(Mixing Step)

In a high-speed stirring-type mixing apparatus, 3.04 parts by weight of a surface crosslinking agent solution (1) consisting of 0.04 part by weight of ethylene glycol diglycidyl ether, 1.0 part by weight of propylene glycol, and 2.0 parts by weight of deionized water was sprayed and added relative to 100 parts by weight of the water absorbent resin powder (1) obtained in Production Example 1, and then uniformly mixed to obtain a mixture (1).

(Reaction Step)

Then, 1000 g of the mixture (1) obtained through the operation was put into a 5-liter batch-type mixer. Before the mixture (1) was put into the batch-type mixer, the batch-type mixer was immersed in an oil bath whose temperature was adjusted in advance to 100° C. After the mixture (1) was put into the batch-type mixer, hot air was let through so that a gas phase temperature and an atmospheric dew point became 100° C. and 75° C., respectively, in the batch-type mixer while the mixture (1) was being stirred with a stirring blade of the mixer, the stirring blade rotating about its shaft at 285 rpm and orbitally rotating at 125 rpm and at a circumferential speed of 3.4 (m/s).

Note that the batch-type mixer was provided with (i) a hot-air ventilation apparatus which lets hot air through, the hot air having an adjusted dew point, (ii) an externally heating apparatus (oil bath) which heats the contents, (iii) a stirring apparatus which stirs the contents, (iv) a temperature measuring apparatus which measures a temperature of the contents, and (v) an inlet via which an aqueous liquid etc. is added. The hot-air ventilation apparatus controlled the gas phase temperature and the atmospheric dew point in the batch-type mixer.

Moreover, the batch-type mixer is favorably correlated with a continuous operation apparatus. This makes it possible to simulate industrial-scale continuous production.

(Addition of Aqueous Liquid in Reaction Step)

In 10 minutes after the mixture (1) was put into the batch-type mixer, 30 g of deionized water (3.0 wt % relative to the water absorbent resin powder (1)) was added via the inlet with a syringe. Note that the mixture (1) had a temperature of 90° C. (that is, the atmospheric dew point+15° C.) and a moisture content of 6.0 wt % immediately before the deionized water was added.

For further 10 minutes after the deionized water was added, operation (reaction) was continued while the temperature of the oil bath, the gas phase temperature, and the atmospheric dew point were being controlled to 100° C., 100° C. and 75° C., respectively. In Example 1, a heat treatment time (retention time) of the mixture (1) in the batch-type mixer was 20 minutes, and the deionized water was added in half of the retention time.

(Sizing Step)

After the reaction step ended, classification was carried out with a JIS standard sieve having a mesh size of 850 μm to obtain a water absorbent resin (1). Note that all particles on the sieve (particles which did not pass through the sieve) were pulverized to pass through the sieve having the mesh size of 850 μm.

The obtained water absorbent resin (1) had an excellent fluidity (Anti-Caking property) during moisture absorption, and contained neither fine powder whose particle diameter was less than 106 μm though 1 wt % of such fine powder existed before the reaction step nor unpulverizable aggregates. The water absorbent resin (1) had a moisture content of 8.5 wt %. Table 1 shows other physical properties of the water absorbent resin (1). The obtained water absorbent resin (1) had a weight average particle diameter (D50) of 450 μm, and contained (i) 99 wt % of a particle whose diameter was not less than 150 μm and less than 850 μm and (ii) 1 wt % of a particle which passes through a sieve having a mesh size of 150 μm (including 0 wt % of a particle which passes through a sieve having a mesh size of 106 μm). Note here that a D50 of the water absorbent resin (1) was 450 μm whereas a particle size (D50) of the non-uniformly pulverized water absorbent resin powder (1) to which the aqueous liquid had not been added was 350 μm. It was found that the water absorbent resin (1) had a mass average particle diameter increase ratio of 22% at which granulation increased a mass average particle diameter. Further, the D50 of the obtained water absorbent resin (1) was 400 μm when impact was applied to the water absorbent resin (1) according to (g) of [Method for measuring physical properties]. It was found that the water absorbent resin (1) had a mass average particle diameter decrease ratio of 11% at which impact decreased the mass average particle diameter.

[Example 2] Addition of Aqueous Liquid in Reaction Step (Atmospheric Dew Point: 65° C., Gas Phase Temperature: 100° C.)

In Example 2 carried out was an operation similar to that carried out in Example 1 except that the atmospheric dew point in a batch-type mixer was controlled to 65° C., so that the following water absorbent resin (2) was obtained. Note that a mixture (2) had a temperature of 90° C. (that is, the atmospheric dew point+25° C.) and a moisture content of 5.1 wt % immediately before deionized water was added during the reaction step.

Similar to Example 1, for further 10 minutes after the deionized water was added in the reaction step, operation (reaction) was continued while an oil bath temperature, the gas phase temperature, and the atmospheric dew point were being controlled to 100° C., 100° C. and 65° C., respectively.

The obtained water absorbent resin (2) had an excellent fluidity during moisture absorption, and contained neither fine powder (which passed through a sieve having a mesh size of 106 μm) nor unpulverizable aggregates. The water absorbent resin (2) had a moisture content of 6.7 wt %. Table 1 shows other physical properties of the water absorbent resin (2).

[Example 3] Addition of Aqueous Liquid in Reaction Step (Atmospheric Dew Point: 45° C., Gas Phase Temperature: 100° C.)

In Example 3 carried out was an operation similar to that carried out in Example 1 except that the atmospheric dew point in a batch-type mixer was controlled to 45° C., so that the following water absorbent resin (3) was obtained. Note that a mixture (3) had a temperature of 90° C. (that is, the atmospheric dew point+45° C.) and a moisture content of 4.3 wt % immediately before deionized water was added during the reaction step.

Similar to Example 1, for further 10 minutes after the deionized water was added in the reaction step, operation (reaction) was continued while an oil bath temperature, the gas phase temperature, and the atmospheric dew point were being controlled to 100° C., 100° C. and 45° C., respectively.

The obtained water absorbent resin (3) had an excellent fluidity during moisture absorption, and contained neither fine powder (which passed through a sieve having a mesh size of 106 μm) nor unpulverizable aggregates. The water absorbent resin (3) had a moisture content of 5.1 wt %. Table 1 shows other physical properties of the water absorbent resin (3).

[Example 4] Addition of Aqueous Liquid in Reaction Step (Atmospheric Dew Point: 85° C., Gas Phase Temperature: 100° C.)

In Example 4 carried out was an operation similar to that carried out in Example 1 except that the atmospheric dew point in a batch-type mixer was controlled to 85° C., so that the following water absorbent resin (4) was obtained. Note that a mixture (4) had a temperature of 90° C. (that is, the atmospheric dew point+5° C.) and a moisture content of 6.8 wt % immediately before deionized water was added during the reaction step.

Similar to Example 1, for further 10 minutes after the deionized water was added in the reaction step, operation (reaction) was continued while an oil bath temperature, the gas phase temperature, and the atmospheric dew point were being controlled to 100° C., 100° C. and 85° C., respectively.

The obtained water absorbent resin (4) had an excellent fluidity during moisture absorption, and contained neither fine powder (which passed through a sieve having a mesh size of 106 μm) nor unpulverizable aggregates. The water absorbent resin (4) had a moisture content of 9.5 wt %. Table 1 shows other physical properties of the water absorbent resin (4).

[Example 5] Addition of Aqueous Liquid in Reaction Step (Atmospheric Dew Point: 75° C., Gas Phase Temperature: 120° C.)

In Example 5 carried out was an operation similar to that carried out in Example 1 except that an oil bath temperature, and the gas phase temperature in a batch-type mixer were controlled to 120° C., so that the following water absorbent resin (5) was obtained. Note that a mixture (5) had a temperature of 110° C. (that is, the atmospheric dew point+35° C.) and a moisture content of 5.7 wt % immediately before deionized water was added during the reaction step.

Similar to Example 1, for further 10 minutes after the deionized water was added in the reaction step, operation (reaction) was continued while the oil bath temperature, the gas phase temperature, and the atmospheric dew point were being controlled to 120° C., 120° C. and 75° C., respectively.

The obtained water absorbent resin (5) had an excellent fluidity during moisture absorption, and contained neither fine powder (which passed through a sieve having a mesh size of 106 μm) nor unpulverizable aggregates. The water absorbent resin (5) had a moisture content of 7.9 wt %. Table 1 shows other physical properties of the water absorbent resin (5).

[Example 6] Addition of Aqueous Liquid in Reaction Step (Quantity of Aqueous Liquid to be Added was Increased to 6.0 Wt %)

In Example 6 carried out was an operation similar to that carried out in Example 1 except that quantity of deionized water to be added was changed to 60 g (6.0 wt % relative to the water absorbent resin powder (1)), so that the following water absorbent resin (6) was obtained. Note that a mixture (6) had a temperature of 90° C. (that is, an atmospheric dew point+15° C.) and a moisture content of 6.0 wt % immediately before the deionized water was added during the reaction step.

For further 10 minutes after 60 g of the deionized water was added in the reaction step, operation (reaction) was continued while an oil bath temperature, a gas phase temperature, and the atmospheric dew point were being controlled to 100° C., 100° C. and 75° C., respectively.

The obtained water absorbent resin (6) had an excellent fluidity during moisture absorption, and contained neither fine powder (which passed through a sieve having a mesh size of 106 μm) nor unpulverizable aggregates. The water absorbent resin (6) had a moisture content of 11.1 wt %. Table 1 shows other physical properties of the water absorbent resin (6).

[Comparative Example 1] No Addition of Aqueous Liquid in Reaction Step

In Comparative Example 1 carried out was an operation similar to that carried out in Example 1 except that deionized water was not added, so that the following comparative water absorbent resin (1) was obtained.

The obtained comparative water absorbent resin (1) had a moisture content of 4.5 wt %. It is guessed that the reason why the moisture content decreased is that any deionized water was not added. Further, 1 wt % of fine powder which existed before the reaction step did not change even after the reaction step but was still as it was. Table 1 shows other physical properties of the comparative water absorbent resin (1).

[Comparative Example 2] Addition of Aqueous Liquid in Reaction Step (Atmospheric Dew Point: 90° C., Gas Phase Temperature: 100° C.)

In Comparative Example 2 carried out was an operation similar to that carried out in Example 1 except that the atmospheric dew point in a batch-type mixer was controlled to 90° C. Note that a comparative mixture (2) had a temperature of 90° C. (that is, a temperature equal to the atmospheric dew point) and a moisture content of 7.0 wt % immediately before 30 g of deionized water was added.

When, similar to Example 1, the deionized water was added in the reaction step, a large number of aggregates of particles were generated, and most of the aggregates adhered to an inner wall of the batch-type mixer. Therefore, operation was stopped. It is guessed that the reason for these is that the atmospheric dew point was increased too much, i.e., up to 90° C. to make no difference between the atmospheric dew point and the temperature (90° C.) of the comparative mixture (2).

[Comparative Example 3] Addition of Aqueous Liquid in Reaction Step (Atmospheric Dew Point: 65° C., Atmospheric Temperature: 70° C.)

In Comparative Example 3 carried out was an operation similar to that carried out in Example 2 except that an oil bath temperature, and a gas phase temperature in a batch-type mixer were controlled to 70° C. Note that a comparative mixture (3) had a temperature of 65° C. (that is, a temperature equal to the atmospheric dew point) and a moisture content of 6.1 wt % immediately before 30 g of deionized water was added.

When, similar to Example 2, the deionized water was added in the reaction step, a large number of aggregates of particles were generated, and most of the aggregates adhered to an inner wall of the batch-type mixer. Therefore, operation was stopped. It is guessed that the reason for these is that the temperature of the comparative mixture (3) to which the deionized water was to be added was decreased too much to make no difference between the atmospheric dew point and the temperature (65° C.) of the comparative mixture (3).

[Example 7] Addition of Aqueous Liquid in Reaction Step (Atmospheric Dew Point: 25° C., Gas Phase Temperature: 70° C.)

In Example 7 carried out was an operation similar to that carried out in Example 1 except that (i) an oil bath temperature, the gas phase temperature in a batch-type mixer, and the atmospheric dew point in the batch-type mixer were controlled to 70° C., 70° C. and 25° C., respectively and (ii) quantity of deionized water to be added was changed to 10 g (1.0 wt % relative to the water absorbent resin powder (1)), so that the following water absorbent resin (7) was obtained. Note that a mixture (7) had a temperature of 65° C. (that is, the atmospheric dew point+40° C.) and a moisture content of 5.9 wt % immediately before the deionized water was added during the reaction step.

For further 10 minutes after 10 g of the deionized water was added in the reaction step, operation (reaction) was continued while the oil bath temperature, the gas phase temperature, and the atmospheric dew point were being controlled to 70° C., 70° C. and 25° C., respectively.

The obtained water absorbent resin (7) had an excellent fluidity during moisture absorption, and contained neither fine powder (which passed through a sieve having a mesh size of 106 μm) nor unpulverizable aggregates. The water absorbent resin (7) had a moisture content of 5.4 wt %. Table 1 shows other physical properties of the water absorbent resin (7).

[Example 8] Addition of Aqueous Liquid in Reaction Step (Atmospheric Dew Point: 45° C., Gas Phase Temperature: 130° C.)

In Example 8 carried out was an operation similar to that carried out in Example 1 except that (i) an oil bath temperature, the gas phase temperature in a batch-type mixer, and the atmospheric dew point in the batch-type mixer were controlled to 140° C., 130° C. and 45° C., respectively and (ii) quantity of deionized water to be added was changed to 60 g (6.0 wt % relative to the water absorbent resin powder (1)), so that the following water absorbent resin (8) was obtained. Note that a mixture (8) had a temperature of 130° C. (that is, the atmospheric dew point+85° C.) and a moisture content of 3.8 wt % immediately before the deionized water was added during the reaction step.

For further 10 minutes after 60 g of the deionized water was added in the reaction step, operation (reaction) was continued while the oil bath temperature, the gas phase temperature, and the atmospheric dew point were being controlled to 140° C., 130° C. and 45° C., respectively.

The obtained water absorbent resin (8) had an excellent fluidity during moisture absorption, and contained neither fine powder (which passed through a sieve having a mesh size of 106 μm) nor unpulverizable aggregates. The water absorbent resin (8) had a moisture content of 5.1 wt %. Table 1 shows other physical properties of the water absorbent resin (8).

[Example 9] Addition of Aqueous Liquid in Reaction Step (Atmospheric Dew Point: 85° C., Gas Phase Temperature: 130° C.)

In Example 9 carried out was an operation similar to that carried out in Example 8 except that the atmospheric dew point in a batch-type mixer was controlled to 85° C., so that the following water absorbent resin (9) was obtained. Note that a mixture (9) had a temperature of 130° C. (that is, the atmospheric dew point+45° C.) and a moisture content of 4.5 wt % immediately before deionized water was added during the reaction step.

For further 10 minutes after 60 g of the deionized water was added in the reaction step, operation (reaction) was continued while an oil bath temperature, the gas phase temperature, and the atmospheric dew point were being controlled to 140° C., 130° C. and 85° C., respectively.

The obtained water absorbent resin (9) had an excellent fluidity during moisture absorption, and contained neither fine powder (which passed through a sieve having a mesh size of 106 μm) nor unpulverizable aggregates. The water absorbent resin (9) had a moisture content of 6.2 wt %. Table 1 shows other physical properties of the water absorbent resin (9).

[Comparative Example 4] Addition of Aqueous Liquid in Reaction Step (Atmospheric Dew Point: 15° C., Gas Phase Temperature: 130° C.)

In Comparative Example 4 carried out was an operation similar to that carried out in Example 8 except that the atmospheric dew point in a batch-type mixer was controlled to 15° C., so that the following comparative water absorbent resin (4) was obtained. Note that a comparative mixture (4) had a temperature of 130° C. (that is, the atmospheric dew point+115° C.) and a moisture content of 3.3 wt % immediately before deionized water was added during the reaction step.

For further 10 minutes after 60 g of the deionized water was added in the reaction step, operation (reaction) was continued while an oil bath temperature, the gas phase temperature, and the atmospheric dew point were being controlled to 140° C., 130° C. and 15° C., respectively.

The obtained comparative water absorbent resin (4) had an excellent fluidity during moisture absorption, and contained neither fine powder (which passed through a sieve having a mesh size of 106 μm) nor unpulverizable aggregates. However, the comparative water absorbent resin (4) had a low moisture content of 4.5 wt %. It is guessed that the reason for such a low moisture content is that the atmospheric dew point in the batch-type mixer was low, and quantity of evaporation increased. Table 1 shows other physical properties of the comparative water absorbent resin (4).

[Example 10] Addition of Aqueous Liquid in Reaction Step (Atmospheric Dew Point: 95° C., Gas Phase Temperature: 170° C.)

In Example 10 carried out was an operation similar to that carried out in Example 1 except that an oil bath temperature, the gas phase temperature in a batch-type mixer, and the atmospheric dew point in the batch-type mixer were controlled to 180° C., 170° C. and 95° C., respectively, so that the following water absorbent resin (10) was obtained. Note that a mixture (10) had a temperature of 160° C. (that is, the atmospheric dew point+55° C.) and a moisture content of 2.7 wt % immediately before deionized water was added during the reaction step.

For further 10 minutes after 30 g of the deionized water was added in the reaction step, operation (reaction) was continued while the oil bath temperature, the gas phase temperature, and the atmospheric dew point were being controlled to 180° C., 170° C. and 95° C., respectively.

The obtained water absorbent resin (10) had an excellent fluidity during moisture absorption, and contained neither fine powder (which passed through a sieve having a mesh size of 106 μm) nor unpulverizable aggregates. However, the water absorbent resin (10) had a remarkably low moisture content of 1.5 wt %. The reason for such a remarkably low moisture content is guessed as follows. The atmospheric dew point in the batch-type mixer was high, i.e., 95° C., and a heating temperature was also high (the temperature of the reactant (10) to which the aqueous liquid was to be added was 160° C.). This increased evaporation of the added aqueous liquid. Table 1 shows other physical properties of the water absorbent resin (10).

[Example 11] Addition of Aqueous Liquid in Reaction Step (Atmospheric Dew Point: 30° C., Gas Phase Temperature: 170° C.)

In Example 11 carried out was an operation similar to that carried out in Example 1 except that an oil bath temperature, the gas phase temperature in a batch-type mixer, and the atmospheric dew point in the batch-type mixer were controlled to 180° C., 170° C. and 30° C., respectively, so that the following water absorbent resin (11) was obtained. Note that a mixture (11) had a temperature of 160° C. (that is, the atmospheric dew point+130° C.) and a moisture content of 2.4 wt % immediately before deionized water was added during the reaction step.

For further 10 minutes after 30 g of the deionized water was added in the reaction step, operation (reaction) was continued while the oil bath temperature, the gas phase temperature, and the atmospheric dew point were being controlled to 180° C., 170° C. and 30° C., respectively.

The obtained water absorbent resin (11) had an excellent fluidity during moisture absorption, and contained neither fine powder (which passed through a sieve having a mesh size of 106 μm) nor unpulverizable aggregates. However, the water absorbent resin (11) had a remarkably low moisture content of 1.0 wt %. The reason for such a remarkably low moisture content is guessed as follows. The atmospheric dew point in the batch-type mixer was low, i.e., 30° C., and a heating temperature was high (the temperature of the reactant (11) to which the aqueous liquid was to be added was 160° C.). This further increased evaporation of the added aqueous liquid. Table 1 shows other physical properties of the water absorbent resin (11).

[Comparative Example 5] No Addition of Aqueous Liquid in Reaction Step

In Comparative Example 5 carried out was an operation similar to that carried out in Example 10 except that deionized water was not added, so that the following comparative water absorbent resin (5) was obtained.

The obtained comparative water absorbent resin (5) had a moisture content of 0.9 wt %. It is guessed that the reason why the moisture content decreased is that any deionized water was not added. Further, 1 wt % of fine powder which existed before the reaction step did not change even after the reaction step but was still as it was. Table 1 shows other physical properties of the comparative water absorbent resin (5).

TABLE 1

Batch-type mixer/Addition of aqueous liquid in reaction step

| | Water absorbent resin powder | Batch-type mixer | | | Mixture (water absorbent resin particle) Immediately before addition of aqueous liquid | | Aqueous liquid (deionized water) | | | Water absorbent resin | | |
|---|---|---|---|---|---|---|---|---|---|---|---|---|---|
| | | Oil bath [° C.] | ADP [° C.] | GPT [° C.] | Temperature [° C.] | MC [wt %] | Added quantity [wt %] | Timing of addition [min] | HTT [min] | | MC [wt %] | CRC [g/g] | AAP [g/g] |
| Ex. 1 | (1) | 100 | 75 | 100 | (1) 90 | 6.0 | 3.0 | 10 | 20 | (1) | 8.5 | 37 | 34 |
| Ex. 2 | (1) | 100 | 65 | 100 | (2) 90 | 5.1 | 3.0 | 10 | 20 | (2) | 6.7 | 38 | 35 |
| Ex. 3 | (1) | 100 | 45 | 100 | (3) 90 | 4.3 | 3.0 | 10 | 20 | (3) | 5.1 | 38 | 35 |
| Ex. 4 | (1) | 100 | 85 | 100 | (4) 90 | 6.8 | 3.0 | 10 | 20 | (4) | 9.5 | 36 | 33 |
| Ex. 5 | (1) | 120 | 75 | 120 | (5) 110 | 5.7 | 3.0 | 10 | 20 | (5) | 7.9 | 37 | 34 |
| Ex. 6 | (1) | 100 | 75 | 100 | (6) 90 | 6.0 | 6.0 | 10 | 20 | (6) | 11.1 | 36 | 33 |
| Com. Ex. 1 | (1) | 100 | 75 | 100 | — | — | — | — | 20 | Com. (1) | 4.5 | 39 | 33 |
| Com. Ex. 2 | (1) | 100 | 90 | 100 | Com. (2) 90 | 7.0 | 3.0 | 10 | — | Stop after addition of aqueous liquid | | | |
| Com. Ex. 3 | (1) | 70 | 65 | 70 | Com. (3) 65 | 6.1 | 3.0 | 10 | — | Stop after addition of aqueous liquid | | | |
| Ex. 7 | (1) | 70 | 25 | 70 | (7) 65 | 5.9 | 1.0 | 10 | 20 | (7) | 5.4 | 38 | 35 |
| Ex. 8 | (1) | 140 | 45 | 130 | (8) 130 | 3.8 | 6.0 | 10 | 20 | (8) | 5.1 | 38 | 35 |
| Ex. 9 | (1) | 140 | 85 | 130 | (9) 130 | 4.5 | 6.0 | 10 | 20 | (9) | 6.2 | 38 | 35 |
| Com. Ex. 4 | (1) | 140 | 15 | 130 | Com. (4) 130 | 3.3 | 6.0 | 10 | 20 | Com. (4) | 4.5 | 39 | 33 |
| Ex. 10 | (1) | 180 | 95 | 170 | (10) 160 | 2.7 | 3.0 | 10 | 20 | (10) | 1.5 | 40 | 34 |
| Ex. 11 | (1) | 180 | 30 | 170 | (11) 160 | 2.4 | 3.0 | 10 | 20 | (11) | 1.0 | 40 | 34 |
| Com. Ex. 5 | (1) | 180 | 95 | 170 | — | — | — | — | 20 | Com. (5) | 0.9 | 40 | 34 |

Ex.: Example,
Com. Ex.: Comparative Example,
MC: Moisture Content
ADP: Atmospheric Dew Point,
GPT: Gas Phase Temperature,
HTT: Heat Treatment Time (Conclusion)

From a comparison among Examples 1 through 4 and Comparative Example 2, it is found that it is possible to uniformly mix a water absorbent resin particle with a surface crosslinking agent by setting a temperature of the water absorbent resin particle to which the aqueous liquid has not been added at a temperature higher than an atmospheric dew point, and it is possible to consequently obtain a water absorbent resin having a high moisture content. This tendency becomes more remarkable as the difference between the temperature of the water absorbent resin particle and the atmospheric dew point is smaller. On the other hand, no difference between the temperature of the water absorbent resin particle and the atmospheric dew point makes operation difficult.

Comparative Example 3 (temperature of water absorbent resin particle: 65° C., atmospheric dew point: 65° C.) also demonstrates that no difference between the temperature of the water absorbent resin particle and the atmospheric dew point makes operation difficult. This suggests that, in order to obtain the water absorbent resin having the high moisture content, the difference between the atmospheric dew point and the temperature of the water absorbent resin particle to which the aqueous liquid is to be added is significant.

From a comparison among Examples 8 and 9 and Comparative Example 4, it is found that, even in a case where a temperature of a water absorbent resin particle is higher than an atmospheric dew point, the atmospheric dew point when an aqueous liquid is added is inevitably not lower than 20° C., preferably not lower than 50° C., and more preferably not lower than 60° C.

From a comparison among Examples 10 and 11 and Comparative Example 5, it is found that it is possible to add an aqueous liquid even at a high temperature of a water absorbent resin particle. It is further found from Examples 1 through 11 that it is preferable that a temperature of a water absorbent resin particle to which an aqueous liquid is to be added be in a range from 70° C. to 120° C., in order to obtain a water absorbent resin having a high moisture content.

Note that, though Table 1 does not show particle sizes of obtained water absorbent resins, the particle sizes of the water absorbent resins (2) through (11) were substantially equal to that of the water absorbent resin (1). Specifically, the water absorbent resins (2) through (11) each (i) had a weight average particle diameter (D50) of approximately 450 μm, (ii) contained 99 wt % of a particle whose diameter was not less than 150 μm and less than 850 μm, and 1 wt % of a particle which passes through a sieve having a mesh size of 150 μm (including 0 wt % of a particle which passes through a sieve having a mesh size of 106 μm), and (iii) had a D50 of approximately 400 μm after impact was applied. The water absorbent resins (2) through (11) each had (i) a mass average particle diameter increase ratio of approximately 20% at which granulation increased a mass average particle diameter and (ii) a mass average particle diameter decrease ratio of approximately 10% at which impact decreased the mass average particle diameter, as compared to the particle size (D50=350 μm) of the non-uniformly pulverized water absorbent resin powder (1) to which the aqueous liquid had not been added.

Production Example 2

A water absorbent resin was produced with a continuous production apparatus for continuously producing 1000 kg of a water absorbent resin per hour, the continuous production apparatus carrying out a polymerization step, a gel-crushing step, a drying step, a pulverization step, a classification step, a surface crosslinking step, a sizing step, and transportation steps each connecting corresponding ones of the steps to each other. The continuous production apparatus was operated under operation conditions of the steps (later described) to start continuously producing the water absorbent resin. Note that Production Example 2 describes production of water absorbent resin powder which has not been surface-crosslinked.

(Polymerization Step)

Prepared was a monomer aqueous solution (2) in which 0.03 mol % of polyethylene glycol diacrylate (molecular weight: 523) was added as an internal crosslinking agent to a partially neutralized acrylic acid sodium salt aqueous solution (monomer concentration: 43 wt %) (i) containing 70 ppm of p-methoxyphenol (relative to acrylic acid) as a polymerization inhibitor and (ii) having a neutralization ratio of 74 mol %. The monomer aqueous solution (2) was continuously supplied to a polymerization apparatus with a metering pump.

During the continuous supply, nitrogen gas was continuously blown into the polymerization apparatus so that not more than 0.5 (mg/l) of oxygen dissolved in the monomer aqueous solution (2). Thereafter, 0.12 (g/mol) of sodium persulfate was continuously added as a polymerization initiator by means of line mixing.

Then, the monomer aqueous solution (2) was supplied onto a planar steel belt (polymerization apparatus) having dams in opposite sides so as to have a thickness of approximately 25 mm, and was statically polymerized for 30 minutes. Through this operation obtained was a strip-shaped water-containing gel-like crosslinked polymer (hydrogel) (2).

(Gel-Crushing Step)

The hydrogel (2) obtained in the polymerization step was supplied to a meat chopper having holes whose diameter was 7 mm, and gel-crushed into particles whose diameter was approximately 2 mm, so that a particulate hydrogel (2) was obtained.

(Drying Step)

The particulate hydrogel (2) was spread on a moving porous plate of a continuous ventilation band-type dryer so as to have a thickness of 50 mm, and dried at 160° C. to 180° C. for 30 minutes. A dried polymer (2) in the form of a block was obtained at an outlet of the dryer.

(Pulverization Step and Classification Step)

All of the dried polymer (2) was continuously pulverized with a three-stage roll mill (roll gap: 1.0 mm, 0.65 mm, and 0.42 mm from the above), and then continuously classified with a classification apparatus provided with metal sieves whose mesh sizes were 850 μm and 150 μm, respectively. Note that the pulverized dried polymer (2) to be introduced to the classification step had a temperature of approximately 60° C.

Through the series of operations obtained was non-uniformly pulverized water absorbent resin powder (2) (i) having a weight average particle diameter (D50) of 350 μm and (ii) containing 95 wt % of a particle whose diameter was not less than 150 μm and less than 850 μm and 5 wt % of a particle which passes through a sieve having a mesh size of 150 μm (including 1 wt % of a particle which passes through a sieve having a mesh size of 106 μm). The obtained water absorbent resin powder (2) had a water absorption capacity without load (CRC) of 51 (g/g) and a moisture content of 4.0 wt %.

[Example 12] Addition of Aqueous Liquid in Reaction Step (Atmospheric Dew Point: 75° C., Gas Phase Temperature: 120° C.)

The continuous production apparatus for producing a water absorbent resin was operated to carry out the surface crosslinking step and subsequent steps following Production Example 2.

(Mixing Step)

The water absorbent resin powder (2) obtained in Production Example 2 was continuously supplied to a high-speed mixing apparatus (Turbulizer/1000 rpm) at 1000 (kg/hr). In the high-speed mixing apparatus, a surface crosslinking agent solution (12) consisting of 0.04 part by weight of ethylene glycol diglycidyl ether, 1.0 part by weight of propylene glycol, and 2.0 parts by weight of deionized water was sprayed relative to 100 parts by weight of the water absorbent resin powder (2) with a spray, and uniformly mixed, so that a mixture (12) was obtained.

(Reaction Step)

The mixture (12) obtained in the mixing step was continuously supplied to a paddle-type and low speed stirring-type indirect heat dryer (paddle dryer), and reacted. In the reaction, the gas phase temperature and the atmospheric dew point, in the paddle dryer, and a heat medium temperature of the paddle dryer, were controlled to 120° C., 75° C. and 100° C., respectively. Note that timing when the mixture (12) was supplied to the paddle dryer was regarded as timing when the reaction started.

In 10 minutes after the reaction started, that is, at a location of forward half of the whole length of the paddle dryer, 250 (g/min) of deionized water (1.5 wt % relative to the water absorbent resin powder (2)) was sprayed and added over the mixture (12) from above during the reaction step. Note that the mixture (12) had a temperature of 95° C. (i.e., the atmospheric dew point+20° C.) and a moisture content of 6.0 wt % immediately before the deionized water was added.

The mixture (12) to which the deionized water had been added formed no aggregate (lump) in the paddle dryer, and was exhausted from an outlet in a dry and smooth state.

(Sizing Step)

After the reaction step ended, classification was carried out with a JIS standard sieve having a mesh size of 850 um, so that a water absorbent resin (12) was obtained. Note that all particles on the sieve (particles which did not pass through the sieve) were pulverized to pass through the sieve having the mesh size of 850 μm.

The obtained water absorbent resin (12) had an excellent fluidity during moisture absorption, and contained neither fine powder (which passed through a sieve having a mesh size of 106 μm) nor aggregates unpulverizable in the sizing step. The water absorbent resin (12) had a moisture content of 6.8 wt %. Table 2 shows other physical properties of the water absorbent resin (12). The obtained water absorbent resin (12) had a weight average particle diameter (D50) of 400 μm, and contained (i) 99 wt % of a particle whose diameter was not less than 150 μm and less than 850 μm and (ii) 1 wt % of a particle which passes through a sieve having a mesh size of 150 μm (including 0 wt % of a particle which passes through a sieve having a mesh size of 106 μm). Note here that the D50 of the water absorbent resin (12) was 400 μm, whereas a particle size (D50) of the non-uniformly pulverized water absorbent resin powder (2) to which an aqueous liquid had not been added was 350 μm. It was found that the water absorbent resin (12) had a mass average particle diameter increase ratio of 13% at which granulation increased a mass average particle diameter. Further, the D50 of the obtained water absorbent resin (12) was 370 μm when impact was applied to the water absorbent resin (12) according to (g) of [Method for measuring physical properties]. It was found that the water absorbent resin (12) had a mass average particle diameter decrease ratio of 7.5% at which impact decreased the mass average particle diameter.

[Example 13] Addition of Aqueous Liquid in Reaction Step (Quantity of Aqueous Liquid to be Added was Increased to 3.0 wt %)

In Example 13 carried out was an operation similar to that carried out in Example 12 except that quantity of deionized water to be added was changed to 500 (g/min) (3.0 wt % relative to the water absorbent resin powder (2)), so that the following water absorbent resin (13) was obtained. Note that a mixture (13) had a temperature of 95° C. (that is, an atmospheric dew point+20° C.) and a moisture content of 6.0 wt % immediately before the deionized water was added during the reaction step.

The obtained water absorbent resin (13) had an excellent fluidity during moisture absorption, and contained neither fine powder (which passed through a sieve having a mesh size of 106 μm) nor aggregates unpulverizable in the sizing step. The water absorbent resin (13) had a moisture content of 7.2 wt %. Table 2 shows other physical properties of the water absorbent resin (13).

[Example 14] Addition of Aqueous Liquid in Reaction Step (Quantity of Aqueous Liquid to be Added was Increased to 7.0 wt %)

In Example 14 carried out was an operation similar to that carried out in Example 12 except that quantity of deionized water to be added was changed to 1167 (g/min) (7.0 wt % relative to the water absorbent resin powder (2)), so that the following water absorbent resin (14) was obtained. Note that a mixture (14) had a temperature of 95° C. (that is, an atmospheric dew point+20° C.) and a moisture content of 6.0 wt % immediately before the deionized water was added during the reaction step.

The obtained water absorbent resin (14) had an excellent fluidity during moisture absorption, and contained neither fine powder (which passed through a sieve having a mesh size of 106 μm) nor aggregates unpulverizable in the sizing step. The water absorbent resin (14) had a moisture content of 9.6 wt %, a degradable soluble component of 22.2 wt %, and a deodorization performance of 3.7. Table 2 shows other physical properties of the water absorbent resin (14).

[Example 15] Addition of Aqueous Liquid in Reaction Step (Quantity of Aqueous Liquid to be Added was Increased to 11.0 wt %)

In Example 15 carried out was an operation similar to that carried out in Example 12 except that quantity of deionized water to be added was changed to 1833 (g/min) (11.0 wt % relative to the water absorbent resin powder (2)), so that the following water absorbent resin (15) was obtained. Note that a mixture (15) had a temperature of 95° C. (that is, an atmospheric dew point+20° C.) and a moisture content of 6.0 wt % immediately before the deionized water was added during the reaction step.

The obtained water absorbent resin (15) had an excellent fluidity during moisture absorption, and contained neither fine powder (which passed through a sieve having a mesh size of 106 μm) nor aggregates unpulverizable in the sizing step. The water absorbent resin (15) had a moisture content of 12.5 wt %. Table 2 shows other physical properties of the water absorbent resin (15).

[Example 16] Addition of Aqueous Liquid in Reaction Step (Quantity of Aqueous Liquid to be Added was Increased to 15.0 wt %)

In Example 16 carried out was an operation similar to that carried out in Example 12 except that quantity of deionized water to be added was changed to 2500 (g/min) (15.0 wt % relative to the water absorbent resin powder (2)). Note that a mixture (16) had a temperature of 95° C. and a moisture content of 6.0 wt % immediately before the deionized water was added during the reaction step.

When the deionized water was added, aggregates of particles were generated, and some of the aggregates adhered to an inner wall of a paddle dryer. This made a long-term operation slightly difficult. It is guessed that the reason for these is that too much deionized water was added.

[Example 17] Addition of Aqueous Liquid in Reaction Step (Change in Location where Aqueous Liquid is Added)

In Example 17 carried out was an operation similar to that carried out in Example 13 except that deionized water was added in 5 minutes after a reaction started, i.e., a location where the deionized water was added was changed to a location of forward one-quarter of the whole length of a paddle dryer, so that the following water absorbent resin (17) was obtained. Note that a mixture (17) had a temperature of 90° C. which was increasing (that is, an atmospheric dew point+15° C.) and a moisture content of 6.1 wt % immediately before the deionized water was added during the reaction step.

The obtained water absorbent resin (17) had an excellent fluidity during moisture absorption, and contained neither fine powder (which passed through a sieve having a mesh size of 106 μm) nor aggregates unpulverizable in the sizing step. The water absorbent resin (17) had a moisture content of 6.6 wt %. Table 2 shows other physical properties of the water absorbent resin (17).

[Example 18] Addition of Aqueous Liquid in Reaction Step (Change in Location where Aqueous Liquid is Added)

In Example 18 carried out was an operation similar to that carried out in Example 13 except that deionized water was added in 15 minutes after a reaction started, i.e., a location where the deionized water was added was changed to a location of forward three-quarter of the whole length of a paddle dryer, so that the following water absorbent resin (18) was obtained. Note that a mixture (18) had a temperature of 98° C. (that is, an atmospheric dew point+23° C.) and a moisture content of 5.9 wt % immediately before the deionized water was added during the reaction step.

The obtained water absorbent resin (18) had an excellent fluidity during moisture absorption, and contained neither fine powder (which passed through a sieve having a mesh size of 106 μm) nor aggregates unpulverizable in the sizing step. The water absorbent resin (18) had a moisture content of 7.5 wt %. Table 2 shows other physical properties of the water absorbent resin (18).

[Comparative Example 6] No Addition of Aqueous Liquid in Reaction Step

In Comparative Example 6 carried out was an operation similar to that carried out in Example 12 except that deionized water was not added, so that the following comparative water absorbent resin (6) was obtained. Note that a comparative mixture (6) formed no aggregates (lumps) in a paddle dryer, and was exhausted from an outlet in a dry and smooth state.

The obtained comparative water absorbent resin (6) had a moisture content of 4.4 wt %. It is guessed that the reason why the moisture content decreased is that any deionized water was not added. Table 2 shows other physical properties of the comparative water absorbent resin (6).

[Example 19] Addition of Aqueous Liquid in Reaction Step (Atmospheric Dew Point: 45° C., Gas Phase Temperature: 120° C.)

In Example 19 carried out was an operation similar to that carried out in Example 14 except that the atmospheric dew point in a paddle dryer was controlled to 45° C., so that the following water absorbent resin (19) was obtained. Note that a mixture (19) had a temperature of 95° C. (that is, the atmospheric dew point+50° C.) and a moisture content of 4.3 wt % immediately before deionized water was added during the reaction step.

The obtained water absorbent resin (19) had an excellent fluidity during moisture absorption, and contained neither fine powder (which passed through a sieve having a mesh size of 106 μm) nor aggregates unpulverizable in the sizing step. The water absorbent resin (19) had a moisture content of 5.8 wt %. Table 2 shows other physical properties of the water absorbent resin (19).

[Example 20] Addition of Aqueous Liquid in Cooling Step (Atmospheric Dew Point: 26° C., Gas Phase Temperature: 60° C.)

The continuous production apparatus for producing a water absorbent resin was operated to carry out the surface crosslinking step and subsequent steps following Production Example 2.

(Mixing Step)

The water absorbent resin powder (2) obtained in Production Example 2 was continuously supplied to a high-speed mixing apparatus (Turbulizer/1000 rpm) at 1000 (kg/hr). In the high-speed mixing apparatus, a surface crosslinking agent solution (20) consisting of 0.04 part by weight of ethylene glycol diglycidyl ether, 1.0 part by weight of propylene glycol, and 2.0 parts by weight of deionized water was sprayed relative to 100 parts by weight of the water absorbent resin powder (2) with a spray, and uniformly mixed, so that a mixture (20) was obtained.

(Reaction Step)

The mixture (12) obtained in the mixing step was continuously supplied to a paddle-type and low speed stirring-type indirect heat dryer (paddle dryer), and reacted. In the reaction, a gas phase temperature and an atmospheric dew point, in the paddle dryer, and a heat medium temperature of the paddle dryer were controlled to 120° C., 75° C. and 100° C., respectively. The mixture (12) formed no aggregates (lumps) in the paddle dryer, and was exhausted in a dry and smooth state. Note that a reactant (20) at an outlet of the paddle dryer had a temperature of 100° C. and a moisture content of 4.4 wt %.

(Cooling Step)

The reactant (20) obtained in the reaction step was continuously supplied to a paddle-type and low speed stirring-type indirect cooling apparatus (paddle cooler) connected in series with the paddle dryer, and was cooled. Specifically, the reactant (20) was cooled by causing warm water of 60° C. to pass through the paddle cooler. A gas phase temperature and an atmospheric dew point, in the paddle cooler, were 60° C. and 26° C., respectively. Note that timing when the reactant (20) was supplied to the paddle cooler was regarded as timing when the cooling started.

In 6.7 minutes after the cooling started, that is, at a location of forward one-third of the whole length of the paddle cooler, 250 (g/min) of deionized water (1.5 wt % relative to the water absorbent resin powder (2)) was sprayed and added from above over the reactant (20) during the cooling step. Note that the reactant (20) had a temperature of 65° C. (i.e., the atmospheric dew point+39° C.) and a moisture content of 4.3 wt % immediately before the deionized water was added.

(Sizing Step)

After the cooling step ended, classification was carried out with a JIS standard sieve having a mesh size of 850 um, so that a water absorbent resin (20) was obtained. Note that all particles on the sieve (particles which did not pass through the sieve) were pulverized to pass through the sieve having the mesh size of 850 μm.

The obtained water absorbent resin (20) had an excellent fluidity during moisture absorption, and contained neither fine powder (which passed through a sieve having a mesh size of 106 μm) nor aggregates unpulverizable in the sizing step. The water absorbent resin (20) had a moisture content of 5.3 wt %. Table 2 shows other physical properties of the water absorbent resin (20).

[Comparative Example 7] No Addition of Aqueous Liquid in Cooling Step

In Comparative Example 7 carried out was an operation similar to that carried out in Example 20 except that deionized water was not added, so that the following comparative water absorbent resin (7) was obtained. Note that a comparative reactant (7) formed no aggregates (lumps) in a paddle dryer, and was exhausted from an outlet in a dry and smooth state.

The obtained comparative water absorbent resin (7) had a moisture content of 4.1 wt %. It is guessed that the reason why the moisture content decreased is that any deionized water was not added. Table 2 shows other physical properties of the comparative water absorbent resin (7).

[Example 21] Addition of Aqueous Liquid in Cooling Step (Atmospheric Dew Point: 36° C., Gas Phase Temperature: 80° C., Quantity of Aqueous Liquid to be Added was Increased to 3.0 Wt %)

In Example 21 carried out was an operation similar to that carried out in Example 20 except that (i) a temperature of warm water to pass through a paddle cooler was changed to 80° C. and (ii) quantity of deionized water to be added was changed to 500 (g/min) (3.0 wt % relative to the water absorbent resin powder (2)), so that the following water absorbent resin (21) was obtained. In the operation of Example 21, the gas phase temperature and the atmospheric dew point, in the paddle cooler, were 80° C. and 36° C., respectively. Note that a reactant (21) had a temperature of 85° C. (that is, the atmospheric dew point+49° C.) and a moisture content of 4.1 wt % immediately before the deionized water was added during the cooling step.

The obtained water absorbent resin (21) had an excellent fluidity during moisture absorption, and contained neither fine powder (which passed through a sieve having a mesh size of 106 μm) nor aggregates unpulverizable in the sizing step. The water absorbent resin (21) had a moisture content of 5.7 wt %. Table 2 shows other physical properties of the water absorbent resin (21).

[Comparative Example 8] Addition of Aqueous Liquid in Cooling Step (Atmospheric Dew Point: 17° C., Gas Phase Temperature: 60° C.)

In Comparative Example 8 carried out was an operation similar to that carried out in Example 20 except that, in a reaction step, a heat medium temperature of a paddle dryer, and a gas phase temperature and an atmospheric dew point, in the paddle dryer, were controlled to 200° C., 180° C. and 95° C., respectively, so that the gas phase temperature and the atmospheric dew point in the paddle cooler were 60° C. and 17° C., respectively. Consequently, the following comparative water absorbent resin (8) was obtained.

A comparative mixture (8) formed no aggregates (lumps) in the paddle dryer, and was exhausted in a dry and smooth state. Note that a comparative reactant (8) at an outlet of the paddle dryer had a temperature of 180° C. and a moisture content of 1.0 wt %.

The comparative reactant (8) had a temperature of 65° C. (that is, the atmospheric dew point+48° C.) and a moisture content of 1.0 wt % immediately before deionized water was added during the cooling step.

The obtained comparative water absorbent resin (8) had an excellent fluidity during moisture absorption, and contained neither fine powder (which passed through a sieve having a mesh size of 106 μm) nor aggregates unpulverizable in the sizing step. However, the comparative water absorbent resin (8) had a low moisture content of 2.1 wt %. It is guessed that the reason for such a low moisture content is that the atmospheric dew point was low, i.e., 17° C. when the aqueous liquid was added. Table 2 shows other physical properties of the comparative water absorbent resin (8).

[Comparative Example 9] Addition of Aqueous Liquid in Cooling Step (Quantity of Aqueous Liquid to be Added was Increased to 3.0 wt %)

In Comparative Example 9 carried out was an operation similar to that carried out in Comparative Example 8 except that quantity of deionized water to be added was changed to 500 (g/min) (3.0 wt % relative to the water absorbent resin powder (2)) in order to increase moisture content of a water absorbent resin. Note that a comparative reactant (9) had a temperature of 65° C. (that is, an atmospheric dew point+48° C.) and a moisture content of 1.0 wt % immediately before the deionized water was added during the cooling step.

When the deionized water was added in the cooling step, aggregates of particles were generated, and curing did not complete at an outlet of a paddle cooler. It is guessed that the reason for these is that the atmospheric dew point was low, i.e., 17° C. when the aqueous solution was added.

[Example 22] Addition of Chelating Agent-Containing Aqueous Liquid in Reaction Step In Example 22 carried out was an operation similar to that carried out in Example 14 except that the deionized water of Example 14 was changed to a chelating agent-containing aqueous liquid that contained 0.53 wt % of a 45 wt % diethylenetriamine pentaacetic acid sodium aqueous solution, so that the following water absorbent resin (22) was obtained. Note that a mixture (22) had a temperature of 95° C. (that is, an atmospheric dew point+20° C.) and a moisture content of 6.0 wt % immediately before the aqueous liquid was added during the reaction step.

The obtained water absorbent resin (22) had an excellent fluidity during moisture absorption, and contained neither fine powder (which passed through a sieve having a mesh size of 106 μm) nor aggregates unpulverizable in the sizing step. The water absorbent resin (22) had a moisture content of 9.6 wt % and a degradable soluble component of 16.7 wt %. Table 2 shows other physical properties of the water absorbent resin (22).

[Example 23] Addition of Deodorant-Containing Aqueous Liquid in Reaction Step In Example 23 carried out was an operation similar to that carried out in Example 14 except that the deionized water of Example 14 was changed to a deodorant-containing aqueous liquid that contained 0.5 wt % of a 15 wt % extract aqueous solution, the extract having been extracted from a leaf of a plant belonging to camellia family (NI-Fresce800MO manufactured by Shiraimatsu Pharmaceutical Co., Ltd.), so that the following water absorbent resin (23) was obtained. Note that a mixture (23) had a temperature of 95° C. (that is, an atmospheric dew point+20° C.) and a moisture content of 6.0 wt % immediately before the aqueous liquid was added during the reaction step.

The obtained water absorbent resin (23) had an excellent fluidity during moisture absorption, and contained neither fine powder (which passed through a sieve having a mesh size of 106 μm) nor aggregates unpulverizable in the sizing step. The water absorbent resin (23) had a moisture content of 9.6 wt % and a deodorization performance of 2.3. Table 2 shows other physical properties of the water absorbent resin (23).

[Example 24] Addition of Aqueous Liquid in Reaction Step and in Cooling Step The continuous production apparatus for producing a water absorbent resin was operated to carry out the surface crosslinking step and subsequent steps following Production Example 2.

(Mixing Step)

The water absorbent resin powder (2) obtained in Production Example 2 was continuously supplied to a high-speed mixing apparatus (Turbulizer/1000 rpm) at 1000 (kg/hr). In the high-speed mixing apparatus, a surface crosslinking agent solution (24) consisting of 0.04 part by weight of ethylene glycol diglycidyl ether, 1.0 part by weight of propylene glycol, and 2.0 parts by weight of deionized water was sprayed relative to 100 parts by weight of the water absorbent resin powder (2) with a spray, and uniformly mixed, so that a mixture (24) was obtained.

(Reaction Step)

The mixture (24) obtained in the mixing step was continuously supplied to a paddle-type and low speed stirring-type indirect heat dryer (paddle dryer), and reacted. In the reaction, a gas phase temperature and an atmospheric dew point, in the paddle dryer, and a heat medium temperature of the paddle dryer were controlled to 120° C., 75° C. and 100° C., respectively. Note that timing when the mixture (24) was supplied to the paddle dryer was regarded as timing when the reaction started.

In 10 minutes after the reaction started, that is, at a location of forward half of the whole length of the paddle dryer, 250 (g/min) of deionized water (1.5 wt % relative to the water absorbent resin powder (2)) was sprayed and added from above over the mixture (24) during the reaction step. Note that the mixture (24) had a temperature of 95° C. (i.e., the atmospheric dew point+20° C.) and a moisture content of 6.0 wt % immediately before the deionized water was added.

The mixture (24) to which the deionized water had been added formed no aggregate (lump) in the paddle dryer, and was exhausted from an outlet in a dry and smooth state. Note that a reactant (24) at the outlet of the paddle dryer had a temperature of 100° C. and a moisture content of 6.8 wt %.

(Cooling Step)

The reactant (24) obtained in the reaction step was continuously supplied to a paddle-type and low speed stirring-type indirect cooling apparatus (paddle cooler) connected in series with the paddle dryer, and was cooled. Specifically, the reactant (24) was cooled by causing warm water of 60° C. to pass through the paddle cooler. A gas phase temperature and an atmospheric dew point, in the paddle cooler, were 60° C. and 32° C., respectively. Note that timing when the reactant (24) was supplied to the paddle cooler was regarded as timing when the cooling started.

In 6.7 minutes after the cooling started, that is, at a location of forward one-third of the whole length of the paddle cooler, 250 (g/min) of deionized water (1.5 wt % relative to the water absorbent resin powder (2)) was sprayed and added from above over the reactant (24) during the cooling step. Note that the reactant (24) had a temperature of 65° C. (i.e., the atmospheric dew point+33° C.) and a moisture content of 6.6 wt % immediately before the deionized water was added.

(Sizing Step)

After the cooling step ended, classification was carried out with a JIS standard sieve having a mesh size of 850 um, so that a water absorbent resin (24) was obtained. Note that all particles on the sieve (particles which did not pass through the sieve) were pulverized to pass through the sieve having the mesh size of 850 μm.

The obtained water absorbent resin (24) had an excellent fluidity during moisture absorption, and contained neither fine powder (which passed through a sieve having a mesh size of 106 μm) nor aggregates unpulverizable in the sizing step. The water absorbent resin (24) had a moisture content of 7.6 wt %. Table 2 shows other physical properties of the water absorbent resin (24).

[Example 25] (Addition of Aqueous Liquid in Step Other than Cooling Step after Reaction Step)

In Example 25 carried out was an operation similar to that carried out in Example 20 except that the paddle cooler of Example 20 was changed to a high-speed mixing apparatus (Turbulizer/1000 rpm), so that the following water absorbent resin (25) was obtained.

In this high-speed mixing apparatus, 250 (g/min) of deionized water (1.5 wt % relative to the water absorbent resin powder (2)) was sprayed and added from above over a reactant (25). At this time, a gas phase temperature and an atmospheric dew point, in the high-speed mixing apparatus, were 75° C. and 62° C., respectively. Note that the reactant (25) in the high-speed mixing apparatus had a temperature of 92° C. (i.e., the atmospheric dew point+30° C.) and a moisture content of 4.4 wt % immediately before the deionized water was added.

When the deionized water was added in the high-speed mixing apparatus, some aggregates of particles were generated. These aggregates did not disturb continuous operation of the high-speed mixing apparatus. However, a curing step (heat treatment at 60° C. for 30 minutes) was required to give fluidity to the water absorbent resin (25).

TABLE 2

Addition of aqueous liquid in continuous reaction step or in continuous cooling step

| | Water absorbent resin powder | Paddle dryer (paddle cooler) | | | Mixture (reactant) (water absorbent resin particle) Immediately before addition of aqueous liquid | | Aqueous liquid (deionized water) | | Water absorbent resin | | | |
|---|---|---|---|---|---|---|---|---|---|---|---|---|
| | | HMT [° C.] | ADP [° C.] | GPT [° C.] | | Temperature [° C.] | MC [wt %] | Added quantity [g/min] | Added location [—] | | MC [wt %] | CRC [g/g] | AAP [g/g] |
| Ex. 12 | (2) | 100 | 75 | 120 | (12) | 95 | 6.0 | 250 | ½ | (12) | 6.8 | 37 | 34 |
| Ex. 13 | (2) | 100 | 75 | 120 | (13) | 95 | 6.0 | 500 | ½ | (13) | 7.2 | 37 | 33 |
| Ex. 14 | (2) | 100 | 75 | 120 | (14) | 95 | 6.0 | 1167 | ½ | (14) | 9.6 | 36 | 33 |
| Ex. 15 | (2) | 100 | 75 | 120 | (15) | 95 | 6.0 | 1833 | ½ | (15) | 12.5 | 35 | 32 |
| Ex. 16 | (2) | 100 | 75 | 120 | (16) | 95 | 6.0 | 2500 | ½ | Slightly difficult in long-term operation | | | |
| Ex. 17 | (2) | 100 | 75 | 120 | (17) | 90 | 6.1 | 500 | ¼ | (17) | 6.6 | 37 | 34 |
| Ex. 18 | (2) | 100 | 75 | 120 | (18) | 98 | 5.9 | 500 | ¾ | (18) | 7.5 | 37 | 34 |
| Com. Ex. 6 | (2) | 100 | 75 | 120 | | — | — | — | — | Com. (6) | 4.4 | 39 | 33 |
| Ex. 19 | (2) | 100 | 45 | 120 | (19) | 95 | 4.3 | 1167 | ½ | (19) | 5.8 | 37 | 34 |
| Ex. 20[1)] | (2) | 60 | 26 | 60 | (20) | 65 | 4.3 | 250 | ⅓ | (20) | 5.3 | 38 | 32 |
| Com. Ex. 7[1)] | (2) | 60 | 26 | 60 | | — | — | — | — | Com. (7) | 4.1 | 39 | 33 |
| Ex. 21[1)] | (2) | 80 | 36 | 80 | (21) | 85 | 4.1 | 500 | ⅓ | (21) | 5.7 | 38 | 32 |
| Com. Ex. 8[1)] | (2) | 60 | 17 | 60 | Com. (8) | 65 | 1.0 | 250 | ⅓ | Com. (8) | 2.1 | 38 | 32 |
| Com. Ex. 9[1)] | (2) | 60 | 17 | 60 | Com. (9) | 65 | 1.0 | 500 | ⅓ | Stop after addition of aqueous liquid | | | |
| Ex. 22 | (2) | 100 | 75 | 120 | (22) | 95 | 6.0 | 1167[2)] | ½ | (22) | 9.6 | 36 | 32 |
| Ex. 23 | (2) | 100 | 75 | 120 | (23) | 95 | 6.0 | 1167[3)] | ½ | (23) | 9.6 | 36 | 32 |
| Ex. 24[4)] | (2) | 100 | 75 | 120 | (24) | 95 | 6.0 | 250 | ½ | (24) | 6.8 | 37 | 34 |
| | (2) | 60 | 32 | 60 | (24) | 65 | 6.6 | 250 | ⅓ | (24) | 7.6 | 37 | 34 |
| Ex. 25[5)] | (2) | — | 62 | 75 | (25) | 92 | 4.4 | 250 | — | Further curing is necessary | | | |

Ex.: Example,
Com. Ex.: Comparative Example,
HMT: Heat Medium Temperature,
ADP: Atmospheric Dew Point,
GPT: Gas Phase Temperature,
MC: Moisture Content,
HTT: Heat Treatment Time
[1)]Addition of deionized water in cooling step (paddle cooler)
[2)]Deionized water was changed to aqueous liquid containing 0.53 wt % of 45 wt % diethylenetriamine pentaacetic acid sodium aqueous solution
[3)]Deionized water was changed to aqueous liquid containing 0.5 wt % of 15 wt % extract aqueous solution, the extract having been extracted from leaf of plant belonging to camellia family
[4)]Addition of deionized water in reaction step (paddle dryer) and in cooling step (paddle cooler). Upper row: paddle dryer, lower row: paddle cooler
[5)]Addition of deionized water in mixing apparatus (Turbulizer)

(Conclusion)

From a comparison among Examples 12 through 16 and Comparative Example 6, it is found that, in a case where quantity of an aqueous liquid to be added relative to water absorbent resin powder is in a range from 1.5 wt % to 11.0 wt % (Examples 12 through 15), the aqueous liquid can be uniformly added to the water absorbent resin powder, whereas in a case where the quantity is increased to 15.0 wt % (Example 16), a long-term operation becomes slightly difficult. From a comparison among Examples 13, 17 and 18, it is found that it is possible to obtain a water absorbent resin having a high moisture content by adding an aqueous liquid late (by shortening a time period after the aqueous liquid is added).

From Comparative Examples 8 and 9, it is found that, even in a case where a temperature of a water absorbent resin particle is higher than an atmospheric dew point, the atmospheric dew point should be not lower than 20° C. when an aqueous liquid is added.

From Examples 22 and 23 in comparison to Example 14, it is found that it is possible to give an additional function to a water absorbent resin while keeping high moisture content and physical properties (CRC and AAP), by adding an additive (a chelating agent or a deodorant) to an aqueous liquid.

From Example 24 in comparison to Example 12 where an aqueous liquid was added in the reaction step, it is found that it is possible to further improve moisture content by further adding an aqueous liquid after the reaction step.

From Example 25, it is found that an aqueous liquid can be added in a step other than the cooling step after the reaction step. From a comparison between Examples 12 through 24 and Example 25, it is found that, in a case where an aqueous liquid is added during the reaction step or during the cooling step after the reaction step, it is possible to omit a curing step (heat treatment to cause a water absorbent resin to absorb the aqueous liquid) after the aqueous liquid is added, thereby further simplifying a process.

Note that, though Table 2 does not show particle sizes of obtained water absorbent resins, the particle sizes of the water absorbent resins (13) through (18) were substantially equal to that of the water absorbent resin (12) of Example 12. Specifically, the water absorbent resins (13) through (18) each (i) had a weight average particle diameter (D50) of approximately 400 μm, (ii) contained 99 wt % of a particle whose diameter was not less than 150 μm and less than 850 μm, and 1 wt % of a particle which passes through a sieve having a mesh size of 150 μm (including 0 wt % of a particle which passes through a sieve having a mesh size of 106 μm), and (iii) had a D50 of approximately 370 μm after impact was applied. The water absorbent resins (13) through (18) each had (i) a mass average particle diameter increase ratio of approximately 13% at which granulation increased a mass average particle diameter and (ii) a mass average particle diameter decrease ratio of approximately 8% at which impact decreased the mass average particle diameter, as compared to the particle size (D50=350 μm) of the non-uniformly pulverized water absorbent resin powder (2) to which the aqueous liquid had not been added.

As described in "[6] Distinction from conventional techniques" above, Patent Literatures 1 through 25 and other prior art documents neither disclose at all a dew point when an aqueous liquid is added to a water absorbent resin nor suggest at all (i) the method of the present invention, which controls a dew point when an aqueous liquid is added and (ii) an effect brought about by the method of the present invention. Though Patent Literatures 2, 19, 21 through 23, and 25 disclose a technique for defining a dew point in a drying step of drying a water absorbent resin, in a surface crosslinking step of surface-crosslinking the water absorbent resin, and in a transporting step of transporting the water absorbent resin, these Patent Literatures have not conventionally suggested at all (i) importance of a dew point when an aqueous liquid is added, (ii) importance of a temperature of water absorbent resin powder to be heated and (iii) an effect brought about by controlling the dew point and the temperature.

According to the method of the present invention, it is possible to obtain a water absorbent resin having (i) a high CRC (particularly in a range from 30 to 45 (g/g)) (further in a range from 35 to 40 (g/g)), (ii) a high AAP (in a range from 30 to 40 (g/g)) (further in a range from 31 to 35 (g/g)), and (iii) the total of the CRC and the AAP of not less than 65 (g/g).

INDUSTRIAL APPLICABILITY

A method of the present invention for producing a polyacrylic acid (salt)-based water absorbent resin is applicable to production of, particularly large-scale production of a water absorbent resin. The polyacrylic acid (salt)-based water absorbent resin produced by the present invention is suitably applied to an absorbent body of sanitary products such as disposable diapers.

The invention claimed is:

1. A method for producing a polyacrylic acid (salt)-based water absorbent resin particle, comprising the steps of:
   (a) adding a surface crosslinking agent solution to water absorbent resin powder to obtain a mixture;
   (b) reacting the mixture; and, thereafter
   (c) adding an aqueous liquid that does not contain a surface crosslinking agent to at least one selected from the group consisting of (i) the water absorbent resin powder during the step (b) and (ii) the water absorbent resin powder after the step (b),
   the aqueous liquid selected from the group consisting of an aqueous liquid consisting of water, an aqueous liquid consisting of water and a chelating agent, and an aqueous liquid consisting of water and a deodorant,
   an atmospheric dew point being higher than 60° C. in the step (c), and
   a temperature of the water absorbent resin powder being higher than the atmospheric dew point in the step (c), and the temperature of the water absorbent resin powder being higher than 90° C. and not higher than 150° C. in step (c).

2. The method as set forth in claim 1, wherein the step (c) is carried out during the step (b).

3. The method as set forth in claim 1, wherein the step (c) is carried out with respect to the water absorbent resin powder which exists in a heat reactor or in an active energy ray reactor.

4. The method as set forth in claim 1, wherein the step (c) is carried out after the step (b).

5. The method as set forth in claim 1, wherein the step (c) starts within 3 minutes after the step (b).

6. The method as set forth in claim 1, wherein the step (c) is carried out with respect to the water absorbent resin powder during a cooling step after the step (b).

7. The method as set forth in claim 1, wherein the water absorbent resin powder has a moisture content in a range from 2 wt % to 15 wt % in the step (c).

8. The method as set forth in claim 1, wherein quantity of the aqueous liquid to be added relative to the water absorbent resin powder is in a range from 0.1 wt % to 14 wt %.

9. The method as set forth in claim 1, wherein the polyacrylic acid (salt)-based water absorbent resin particle has a moisture content in a range from 5 wt % to 20 wt %.

10. The method as set forth in claim 1, wherein a mass average particle diameter (D50) increase ratio (%) at which granulation increases a D50 is in a range from 5% to 50%.

* * * * *